United States Patent
Hopkins et al.

(10) Patent No.: US 11,636,548 B1
(45) Date of Patent: *Apr. 25, 2023

(54) METHOD, APPARATUS, AND COMPUTER PROGRAM PRODUCT FOR PROVIDING ESTIMATED PRESCRIPTION COSTS

(71) Applicant: McKesson Corporation, Irving, TX (US)

(72) Inventors: Stacy Hopkins, Loganville, GA (US); Scott Genone, Roswell, GA (US); Mark Beers, Lilburn, GA (US)

(73) Assignee: MCKESSON CORPORATION, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/832,318

(22) Filed: Mar. 27, 2020

Related U.S. Application Data

(63) Continuation-in-part of application No. 16/453,509, filed on Jun. 26, 2019.

(51) Int. Cl.
| | |
|---|---|
| *G06Q 40/08* | (2012.01) |
| *G16H 20/10* | (2018.01) |
| *G06Q 20/38* | (2012.01) |

(52) U.S. Cl.
CPC .......... *G06Q 40/08* (2013.01); *G06Q 20/387* (2013.01); *G16H 20/10* (2018.01)

(58) Field of Classification Search
CPC ........ G16H 20/10; G16H 10/60; G06Q 40/08; G06Q 10/10
See application file for complete search history.

(56) References Cited

U.S. PATENT DOCUMENTS

| | | |
|---|---|---|
| 5,012,035 A | 4/1991 | Sartori et al. |
| 5,173,851 A | 12/1992 | Off et al. |
| 5,595,342 A | 1/1997 | McNair et al. |

(Continued)

FOREIGN PATENT DOCUMENTS

| | | |
|---|---|---|
| AU | 2003243327 A | 12/2003 |
| CA | 2482370 | 3/2006 |

(Continued)

OTHER PUBLICATIONS

USC Schaeffer: Prescription Drug Copayment Coupon Landscape https://healthpolicy.usc.edu/research/prescription-drug-copayment-coupon-landscape/ (Year: 2018).*

(Continued)

*Primary Examiner* — Calvin L Hewitt, II
*Assistant Examiner* — Amanulla Abdullaev
(74) *Attorney, Agent, or Firm* — Alston & Bird LLP

(57) ABSTRACT

A method, apparatus and computer program product are provided for providing a patient with prescribed medication cost information at a point of prescribing. A prescription benefit coverage inquiry is received and provided to a claims processor for processing. Historical data associated with prior prescription transactions is utilized to determine an estimated cost range of a prescribed medication in the event of an insufficient or absent response from a benefits manager. The estimated cost range is then provided to a prescriber to share with a patient. A targeted out-of-pocket cost according to incentives, such as vouchers and drug manufacturer rebates may also be provided.

11 Claims, 4 Drawing Sheets

(56) References Cited

U.S. PATENT DOCUMENTS

| | | |
|---|---|---|
| 5,628,530 A | 5/1997 | Thornton |
| 5,726,092 A | 3/1998 | Mathews et al. |
| 5,757,898 A | 5/1998 | Nishikawa |
| 5,769,228 A | 6/1998 | Wroblewski |
| 6,012,035 A | 1/2000 | Freeman et al. |
| 6,111,218 A | 8/2000 | Akers et al. |
| 6,463,462 B1 | 10/2002 | Smith et al. |
| 6,595,342 B1 | 7/2003 | Maritzen et al. |
| 6,726,092 B2 | 4/2004 | Goldberg et al. |
| 6,757,898 B1 | 6/2004 | Ilsen et al. |
| 6,769,228 B1 | 8/2004 | Mahar |
| 7,155,397 B2 | 12/2006 | Alexander et al. |
| 7,192,741 B2 | 3/2007 | Otte et al. |
| 7,337,129 B1 | 2/2008 | Lowry et al. |
| 7,346,768 B2 | 3/2008 | DiRienzo |
| 7,409,632 B1 | 8/2008 | DiRienzo |
| 7,734,483 B2 | 6/2010 | Smith et al. |
| 7,783,383 B2 | 8/2010 | Eliuk et al. |
| 7,840,424 B2 | 11/2010 | Wiley et al. |
| 7,856,364 B1 | 12/2010 | Wiley et al. |
| 7,912,741 B1 | 3/2011 | Pinsonneault |
| 7,921,021 B1 | 4/2011 | Newman |
| 8,036,913 B1 | 10/2011 | Pinsonneault |
| 8,036,914 B1 | 10/2011 | Pinsonneault |
| 8,036,918 B1 | 10/2011 | Pinsonneault |
| 8,050,943 B1 | 11/2011 | Wiley et al. |
| 8,060,379 B1 | 11/2011 | Pinsonneault et al. |
| 8,326,773 B1 | 12/2012 | Bellamy |
| 8,412,537 B1 * | 4/2013 | Fenton ................ G06Q 10/10 |
| | | 705/2 |
| 8,489,415 B1 * | 7/2013 | Ringold ................ G06Q 10/10 |
| | | 705/2 |
| 8,521,557 B1 | 8/2013 | Ringold et al. |
| 8,560,340 B1 | 10/2013 | Ringold |
| 8,645,162 B2 | 2/2014 | Boerger et al. |
| 8,671,018 B2 | 3/2014 | Thomas et al. |
| 8,738,399 B1 | 5/2014 | Abou Nader et al. |
| 8,786,650 B1 | 7/2014 | Eller et al. |
| 8,984,059 B2 | 3/2015 | Johnson |
| 9,026,507 B2 | 5/2015 | Shraim et al. |
| 9,100,793 B2 | 8/2015 | Johnson |
| 9,171,322 B2 | 10/2015 | Spievak et al. |
| 9,356,947 B2 | 5/2016 | Shraim et al. |
| 9,760,871 B1 | 9/2017 | Pourfallah et al. |
| 10,157,262 B1 | 12/2018 | Pinsonneault |
| 10,417,380 B1 | 9/2019 | Kaye et al. |
| 10,489,552 B2 | 11/2019 | Pinsonneault |
| 10,496,793 B1 | 12/2019 | Lawrence et al. |
| 10,565,656 B1 | 2/2020 | Pinsonneault et al. |
| 10,606,984 B1 | 3/2020 | Kaye et al. |
| 10,616,146 B1 | 4/2020 | Hopkins et al. |
| 10,628,797 B2 | 4/2020 | Shraim et al. |
| 10,642,812 B1 | 5/2020 | Hopkins et al. |
| 10,713,694 B1 | 7/2020 | Harris et al. |
| 10,747,848 B2 | 8/2020 | Guinan |
| 10,778,618 B2 | 9/2020 | Karnin et al. |
| 10,862,832 B1 | 12/2020 | Harris |
| 10,924,545 B2 | 2/2021 | Momchilov et al. |
| 10,924,585 B1 | 2/2021 | Harris et al. |
| 10,929,932 B1 | 2/2021 | Golden et al. |
| 10,978,198 B1 | 4/2021 | Pinsonneault |
| 10,999,224 B1 | 5/2021 | Frechen et al. |
| 2001/0029483 A1 | 10/2001 | Schultz et al. |
| 2001/0037216 A1 | 11/2001 | Oscar et al. |
| 2001/0039589 A1 | 11/2001 | Aho et al. |
| 2001/0056359 A1 | 12/2001 | Abreu |
| 2002/0002495 A1 | 1/2002 | Ullman |
| 2002/0004812 A1 | 1/2002 | Motoyama |
| 2002/0032582 A1 | 3/2002 | Feeney et al. |
| 2002/0032583 A1 | 3/2002 | Joao |
| 2002/0035484 A1 | 3/2002 | McCormick |
| 2002/0087583 A1 | 7/2002 | Morgan et al. |
| 2002/0111832 A1 | 8/2002 | Judge |
| 2002/0147614 A1 | 10/2002 | Doerr et al. |
| 2002/0188552 A1 | 12/2002 | Kavounas et al. |
| 2002/0198831 A1 | 12/2002 | Patricelli et al. |
| 2003/0009367 A1 | 1/2003 | Morrison |
| 2003/0050796 A1 | 3/2003 | Baldwin |
| 2003/0050799 A1 | 3/2003 | Jay et al. |
| 2003/0069760 A1 | 4/2003 | Gelber |
| 2003/0074234 A1 | 4/2003 | Stasny |
| 2003/0097310 A1 | 5/2003 | Ono et al. |
| 2003/0149625 A1 | 8/2003 | Leonardi et al. |
| 2003/0154163 A1 | 8/2003 | Phillips et al. |
| 2003/0172008 A1 * | 9/2003 | Hage ................ G06Q 30/02 |
| | | 705/28 |
| 2003/0187690 A1 | 10/2003 | Miller |
| 2003/0229540 A1 | 12/2003 | Algiene |
| 2003/0236747 A1 | 12/2003 | Sager |
| 2004/0039599 A1 | 2/2004 | Fralic |
| 2004/0054685 A1 | 3/2004 | Rahn et al. |
| 2004/0059607 A1 | 3/2004 | Ball et al. |
| 2004/0073456 A1 | 4/2004 | Gottlieb et al. |
| 2004/0073457 A1 | 4/2004 | Kalies |
| 2004/0078222 A1 | 4/2004 | Khan et al. |
| 2004/0078234 A1 | 4/2004 | Tallal, Jr. |
| 2004/0088187 A1 | 5/2004 | Chudy et al. |
| 2004/0103062 A1 | 5/2004 | Wood et al. |
| 2004/0117323 A1 | 6/2004 | Mindala |
| 2004/0148198 A1 | 7/2004 | Kalies |
| 2004/0153336 A1 | 8/2004 | Virdee et al. |
| 2004/0199545 A1 | 10/2004 | Wagner et al. |
| 2004/0236630 A1 | 11/2004 | Kost et al. |
| 2004/0249745 A1 | 12/2004 | Baaren |
| 2005/0015280 A1 | 1/2005 | Gabel et al. |
| 2005/0060201 A1 | 3/2005 | Connely, III et al. |
| 2005/0075932 A1 | 4/2005 | Mankoff |
| 2005/0080692 A1 | 4/2005 | Padam et al. |
| 2005/0102169 A1 | 5/2005 | Wilson |
| 2005/0154627 A1 | 7/2005 | Zuzek et al. |
| 2005/0187793 A1 | 8/2005 | Myles |
| 2005/0197862 A1 | 9/2005 | Paterson et al. |
| 2005/0240442 A1 | 10/2005 | Lapsker et al. |
| 2005/0240473 A1 | 10/2005 | Ayers, Jr. et al. |
| 2005/0261939 A1 | 11/2005 | Augspurger et al. |
| 2005/0288972 A1 | 12/2005 | Marvin et al. |
| 2006/0020514 A1 | 1/2006 | Yered |
| 2006/0026041 A1 | 2/2006 | Ullman |
| 2006/0036470 A1 | 2/2006 | Oaks |
| 2006/0085231 A1 | 4/2006 | Brofman |
| 2006/0085385 A1 | 4/2006 | Foster et al. |
| 2006/0113376 A1 | 6/2006 | Reed et al. |
| 2006/0149595 A1 | 7/2006 | Williams et al. |
| 2006/0149784 A1 | 7/2006 | Tholl et al. |
| 2006/0184391 A1 | 8/2006 | Barre et al. |
| 2006/0212318 A1 | 9/2006 | Dooley |
| 2006/0212345 A1 | 9/2006 | Soza et al. |
| 2006/0224414 A1 | 10/2006 | Astrup et al. |
| 2006/0224417 A1 | 10/2006 | Werner |
| 2006/0224443 A1 | 10/2006 | Soza et al. |
| 2006/0235747 A1 | 10/2006 | Hammond et al. |
| 2006/0259363 A1 | 11/2006 | Jhetam |
| 2007/0005402 A1 | 1/2007 | Kennedy et al. |
| 2007/0033137 A1 | 2/2007 | Provost et al. |
| 2007/0043589 A1 | 2/2007 | Warren et al. |
| 2007/0043595 A1 * | 2/2007 | Pederson ................ G16H 20/10 |
| | | 705/2 |
| 2007/0050209 A1 | 3/2007 | Yered |
| 2007/0050210 A1 | 3/2007 | Wiley, II |
| 2007/0067186 A1 | 3/2007 | Brenner et al. |
| 2007/0094133 A1 | 4/2007 | Anandarao et al. |
| 2007/0108053 A1 | 5/2007 | Cramer et al. |
| 2007/0136100 A1 | 6/2007 | Daugherty et al. |
| 2007/0162303 A1 | 7/2007 | Wiley et al. |
| 2007/0185799 A1 | 8/2007 | Harrison et al. |
| 2007/0191985 A1 | 8/2007 | Bain |
| 2007/0194352 A1 | 8/2007 | Han |
| 2007/0202886 A1 | 8/2007 | Dhebri et al. |
| 2007/0204043 A1 | 8/2007 | Espinosa et al. |
| 2007/0219813 A1 | 9/2007 | Moore |
| 2007/0233525 A1 | 10/2007 | Boyle |
| 2007/0233526 A1 | 10/2007 | Hoffman et al. |
| 2007/0239493 A1 | 10/2007 | Sweetland et al. |
| 2007/0250341 A1 | 10/2007 | Howe et al. |

(56) References Cited

U.S. PATENT DOCUMENTS

| | | |
|---|---|---|
| 2007/0260750 A1 | 11/2007 | Feied et al. |
| 2007/0276697 A1 | 11/2007 | Wiley et al. |
| 2007/0294765 A1 | 12/2007 | Rihn et al. |
| 2007/0299915 A1 | 12/2007 | Shraim et al. |
| 2008/0033750 A1 | 2/2008 | Swiss et al. |
| 2008/0103836 A1 | 5/2008 | Park et al. |
| 2008/0112411 A1 | 5/2008 | Stafford et al. |
| 2008/0152107 A1 | 6/2008 | Mendiola |
| 2008/0215361 A1 | 9/2008 | Nunnari et al. |
| 2008/0262948 A1 | 10/2008 | Grady et al. |
| 2009/0030719 A1 | 1/2009 | Nadas et al. |
| 2009/0064330 A1 | 3/2009 | Shraim et al. |
| 2009/0094051 A1 | 4/2009 | Ard et al. |
| 2009/0100099 A1 | 4/2009 | Buckwalter |
| 2009/0112707 A1 | 4/2009 | Weiss et al. |
| 2009/0204477 A1 | 8/2009 | Urso |
| 2009/0287558 A1 | 11/2009 | Seth et al. |
| 2009/0313112 A1 | 12/2009 | Champ et al. |
| 2009/0327363 A1 | 12/2009 | Cullen et al. |
| 2010/0030667 A1 | 2/2010 | Chudy et al. |
| 2010/0070298 A1 | 3/2010 | Kalies |
| 2010/0144259 A1 | 6/2010 | Allexon et al. |
| 2010/0145730 A1 | 6/2010 | Abreu |
| 2010/0161353 A1* | 6/2010 | Mayaud ............... G16H 10/60 705/3 |
| 2010/0217622 A1 | 8/2010 | Brown et al. |
| 2010/0285821 A1 | 11/2010 | Smeeding et al. |
| 2010/0293236 A1 | 11/2010 | Wisner et al. |
| 2011/0112871 A1 | 5/2011 | Simonowski et al. |
| 2011/0161109 A1 | 6/2011 | Pinsonneault et al. |
| 2011/0196697 A1 | 8/2011 | Akers |
| 2011/0288925 A1 | 11/2011 | Thomas et al. |
| 2012/0053958 A1 | 3/2012 | Marshall et al. |
| 2012/0136809 A1 | 5/2012 | Cannata et al. |
| 2012/0143627 A1 | 6/2012 | Ruben et al. |
| 2012/0166268 A1 | 6/2012 | Griffiths |
| 2012/0179481 A1 | 7/2012 | Patel et al. |
| 2012/0185263 A1 | 7/2012 | Emert |
| 2012/0185264 A1 | 7/2012 | Demogenes et al. |
| 2012/0253829 A1 | 10/2012 | John et al. |
| 2012/0253830 A1 | 10/2012 | John et al. |
| 2012/0253831 A1 | 10/2012 | John et al. |
| 2012/0253832 A1 | 10/2012 | John et al. |
| 2012/0253833 A1 | 10/2012 | John et al. |
| 2012/0253846 A1* | 10/2012 | John ...................... G16H 40/67 705/2 |
| 2012/0265591 A1 | 10/2012 | Hwang |
| 2013/0041968 A1 | 2/2013 | Cohen et al. |
| 2013/0103602 A1* | 4/2013 | Melnick ............... G06Q 40/08 705/322 |
| 2013/0144715 A1 | 6/2013 | Kranzley et al. |
| 2013/0197980 A1 | 8/2013 | Lerner et al. |
| 2013/0246082 A1 | 9/2013 | Brylawski et al. |
| 2013/0311389 A1 | 11/2013 | Kaehler et al. |
| 2014/0039911 A1 | 2/2014 | Iyer |
| 2014/0088985 A1 | 3/2014 | Grant et al. |
| 2014/0214435 A1 | 7/2014 | Previdi |
| 2014/0249861 A1 | 9/2014 | Gamble et al. |
| 2014/0249864 A1 | 9/2014 | Sultan et al. |
| 2014/0278456 A1 | 9/2014 | Milosevich et al. |
| 2015/0088557 A1 | 3/2015 | Huynh et al. |
| 2015/0142479 A1 | 5/2015 | Porter et al. |
| 2015/0149197 A1 | 5/2015 | Guinan |
| 2015/0154565 A1 | 6/2015 | Kaehler et al. |
| 2015/0154588 A1 | 6/2015 | Purves et al. |
| 2015/0195224 A1 | 7/2015 | Karnin et al. |
| 2015/0213195 A1 | 7/2015 | Blechman |
| 2015/0234991 A1* | 8/2015 | Pinsonneault ......... G06Q 40/08 705/3 |
| 2015/0235177 A1 | 8/2015 | Shraim et al. |
| 2015/0269695 A1 | 9/2015 | Pinsonneault et al. |
| 2015/0332422 A1 | 11/2015 | Gilmartin |
| 2015/0371000 A1* | 12/2015 | Pinsonneault ......... G16H 10/60 705/2 |
| 2016/0012465 A1 | 1/2016 | Sharp |
| 2016/0140593 A1 | 5/2016 | Smeeding et al. |
| 2016/0213512 A1 | 7/2016 | Palanker et al. |
| 2016/0267544 A1 | 9/2016 | Flood et al. |
| 2016/0267545 A1 | 9/2016 | Glass et al. |
| 2016/0307195 A1 | 10/2016 | Cantwell et al. |
| 2016/0358142 A1 | 12/2016 | Hillen |
| 2016/0359795 A1 | 12/2016 | Fehling |
| 2017/0034087 A1 | 2/2017 | Borenstein et al. |
| 2017/0220768 A1 | 8/2017 | Tanner, Jr. et al. |
| 2017/0323295 A1 | 11/2017 | Kranzley et al. |
| 2017/0324695 A1 | 11/2017 | Fischer et al. |
| 2018/0012244 A1 | 1/2018 | Leonardi |
| 2018/0366810 A1 | 12/2018 | Nero et al. |
| 2019/0213212 A1 | 7/2019 | Adato et al. |
| 2019/0385733 A1 | 12/2019 | Kaye et al. |
| 2019/0385734 A1 | 12/2019 | Pinsonneault |
| 2021/0319887 A1 | 10/2021 | Derrick, Jr. et al. |

FOREIGN PATENT DOCUMENTS

| | | |
|---|---|---|
| CA | 2792252 A1 | 4/2013 |
| CA | 2810686 A1 | 10/2013 |
| CN | 102362778 | 2/2012 |
| KR | 100755440 | 9/2007 |
| KR | 100793852 | 1/2008 |
| KR | 101038074 | 6/2011 |
| KR | 101101692 | 12/2011 |
| KR | 20110138108 | 12/2011 |
| KR | 20110138572 | 12/2011 |
| KR | 101154858 | 6/2012 |
| WO | WO 1991/006917 | 5/1991 |
| WO | WO 1995003569 | 2/1995 |
| WO | WO 1997/025682 | 7/1997 |
| WO | WO 1998/050871 | 11/1998 |
| WO | WO 2000039737 | 7/2000 |
| WO | WO 2003/098401 | 11/2003 |
| WO | WO 2007025295 | 3/2007 |
| WO | WO 2007/094772 A1 | 8/2007 |
| WO | WO 2008/092109 | 7/2008 |

OTHER PUBLICATIONS

California Health Care Foundation: When the Price Is Not Right: State Options on Prescription Drug Pricing. https://www.chcf.org/wp-content/uploads/2017/12/PDF-WhenStateRxPricing.pdf (Year: 2016).*

American Hospital Association: Drug Price Proposals https://www.aha.org/system/files/media/file/2019/04/aha-drug-policy-recommendations_2.pdf (Year: 2019).*

Almaro, Moshe; "Recovery and Reuse of Unused Prescription Drugs" MIT What Matters: Aug. 2005.

American Society of Health-System Pharmacists (ASHP), "Is Prescribing the Next Step in the Evolution of Pharmacy?" May 15, 2012.

Consalvo, Bob; "City of Boston in the City Council" hearing notice, Dec. 6, 2006.

Coping will Information Overload. The News Source for Healthcare Information Technology [Online] Nov. 2004. URL: http://www.awarix.com.

Final Office Action for U.S. Appl. No. 15/085,166, dated Dec. 4, 2020, 12 pages.

Final Office Action for U.S. Appl. No. 12/140,015 dated Jan. 31, 2011.

Final Office Action for U.S. Appl. No. 12/415,062 dated Oct. 6, 2011.

Final Office Action for U.S. Appl. No. 12/555,589 dated Apr. 11, 2012.

Final Office Action for U.S. Appl. No. 12/560,071 dated Aug. 28, 2015.

Final Office Action for U.S. Appl. No. 12/560,071 dated Nov. 8, 2012.

Final Office Action for U.S. Appl. No. 12/570,982 dated Apr. 11, 2014.

(56) References Cited

OTHER PUBLICATIONS

Final Office Action for U.S. Appl. No. 12/570,982 dated Aug. 28, 2015.
Final Office Action for U.S. Appl. No. 12/570,982 dated Jan. 17, 2013.
Final Office Action for U.S. Appl. No. 12/730,015 dated Aug. 14, 2012.
Final Office Action for U.S. Appl. No. 12/978,898 dated May 16, 2013.
Final Office Action for U.S. Appl. No. 13/721,890 dated Jun. 24, 2015.
Final Office Action for U.S. Appl. No. 13/721,890 dated Nov. 25, 2016.
Final Office Action for U.S. Appl. No. 13/782,909 dated May 31, 2016.
Final Office Action for U.S. Appl. No. 13/782,909 dated Oct. 6, 2015.
Final Office Action for U.S. Appl. No. 13/804,175 dated Oct. 6, 2015.
Final Office Action for U.S. Appl. No. 14/090,113 dated Jan. 6, 2016.
Final Office Action for U.S. Appl. No. 14/090,122 dated Apr. 22, 2016.
Final Office Action for U.S. Appl. No. 14/193,294 dated May 2, 2016.
Final Office Action for U.S. Appl. No. 14/218,326 dated Jun. 30, 2016.
Kaplan et al., "Let the Needles Do the Talking! Evaluating the New Haven Needle Exchange." Interfaces 23:1, Jan.-Feb. 1993 (pp. 7-26).
Lamb, J., New Era of Electronic Medicine Management: E-Prescriptions, Britain's Traditionally Cautious National Health Service is Starting Trials for Online Prescription, with the Aim of Cutting Costs, Finance Times, London, Feb. 21, 2001, p. 6, London, United Kingdom.
Letter Restarting Period for Response for U.S. Appl. No. 13/721,890 dated Jan. 14, 2015.
Marie Chisholm et al. "Pharmaceutical Manufacturer Assistance Program." Arch Intern Med. vol. 162, Apr. 8, 2002.
Non-Final Office Action for U.S. Appl. No. 13/721,890 dated Jun. 14, 2016.
Non-Final Office Action for U.S. Appl. No. 12/560,071 dated Jun. 21, 2012.
Non-Final Office Action for U.S. Appl. No. 12/570,982 dated Jun. 20, 2012.
Non-Final Office Action for U.S. Appl. No. 14/193,294 dated Feb. 21, 2017.
Non-Final Office Action for U.S. Appl. No. 15/085,166 dated Jun. 12, 2020, 40 pages.
Non-Final Office Action for U.S. Appl. No. 16/180,915 dated Jun. 1, 2020, 40 pages.
Non-final Office Action for U.S. Appl. No. 12/140,015 dated Oct. 8, 2010.
Non-final Office Action for U.S. Appl. No. 12/189,650 dated Jan. 22, 2010.
Non-final Office Action for U.S. Appl. No. 12/189,654 dated Jan. 22, 2010.
Non-Final Office Action for U.S. Appl. No. 12/415,062 dated Mar. 30, 2011.
Non-Final Office Action for U.S. Appl. No. 12/555,589 dated Dec. 9, 2011.
Non-Final Office Action for U.S. Appl. No. 12/560,071 dated Sep. 23, 2014.
Non-Final Office Action for U.S. Appl. No. 12/570,982 dated Sep. 12, 2013.
Non-Final Office Action for U.S. Appl. No. 12/730,015 dated Mar. 6, 2012.
Non-Final Office Action for U.S. Appl. No. 12/956,411 dated Jan. 24, 2011.
Non-Final Office Action for U.S. Appl. No. 12/978,898 dated Feb. 6, 2013.
Non-Final Office Action for U.S. Appl. No. 12/982,395 dated Dec. 11, 2012.
Non-Final Office Action for U.S. Appl. No. 13/721,890 dated Jan. 9, 2015.
Non-final Office Action for U.S. Appl. No. 13/782,909 dated Feb. 11, 2016.
Notice of Allowance for U.S. Appl. No. 16/180,915 dated Dec. 11, 2020, 23 pages.
Notice of Allowance for U.S. Appl. No. 11/674,069 dated Jul. 19, 2010.
Notice of Allowance for U.S. Appl. No. 12/140,015 dated Jun. 10, 2011.
Notice of Allowance for U.S. Appl. No. 12/165,221 dated Nov. 16, 2010.
Notice of Allowance for U.S. Appl. No. 12/189,650 dated Aug. 13, 2010.
Notice of Allowance for U.S. Appl. No. 12/956,411 dated Aug. 5, 2011.
Notice of Allowance for U.S. Appl. No. 12/982,395 dated Apr. 24, 2013.
Notice of Allowance for U.S. Appl. No. 14/181,011 dated May 15, 2019.
Notice of Allowance received for U.S. Appl. No. 14/643,468, dated Oct. 24, 2018.
Notice of Allowance received for U.S. Appl. No. 14/181,011, dated Feb. 13, 2019.
Office Action for U.S. Appl. No. 12/570,982 dated Apr. 8, 2015.
Office Action for U.S. Appl. No. 14/181,011 dated Feb. 29, 2016.
Office Action for U.S. Appl. No. 14/181,011 dated Mar. 20, 2017.
Office Action for U.S. Appl. No. 14/181,011 dated Oct. 20, 2016.
Office Action for U.S. Appl. No. 14/181,011 dated Sep. 12, 2017.
Office Action for U.S. Appl. No. 14/193,294 dated Aug. 4, 2017, 31 pages.
Office Action for U.S. Appl. No. 14/193,294 dated Mar. 22, 2018, 28 pages.
Office Action for U.S. Appl. No. 14/229,043 dated Feb. 27, 2019.
Office Action for U.S. Appl. No. 14/229,043 dated Jul. 24, 2017.
Office Action for U.S. Appl. No. 14/229,043 dated Sep. 5, 2019.
Office Action for U.S. Appl. No. 14/229,043 dated Sep. 14, 2018.
Office Action for U.S. Appl. No. 14/643,468 dated Mar. 8, 2018.
Office Action for U.S. Appl. No. 15/085,166 dated Dec. 27, 2018.
Office Action for U.S. Appl. No. 15/085,166 dated Mar. 3, 2020.
Office Action for U.S. Appl. No. 15/085,166 dated Sep. 4, 2019 23 pages.
Office Action for U.S. Appl. No. 13/782,909 dated Jun. 25, 2015.
Office Action for U.S. Appl. No. 13/804,175 dated Mar. 13, 2015.
Office Action for U.S. Appl. No. 14/090,122 dated Oct. 21, 2016.
Office Action for U.S. Appl. No. 14/090,122 dated Sep. 11, 2015.
Office Action for U.S. Appl. No. 14/1090,113 dated Jun. 18, 2015.
Office Action for U.S. Appl. No. 14/1218,326 dated Dec. 1, 2015.
Office Action for U.S. Appl. No. 14/193,294 dated Dec. 17, 2015.
Opar, Alisa; "Rising drug costs prompt new uses for old pills." Nature Medicine, 1211333 (2006).
Pharmacy Reject Codes NCPDP.
Siller et al., "Safe Disposal of Unused Controlled Substances" Avalere Health 2008.
St. Vincent's first to use Birmingham startup's information system. The Birmingham News [Online] Apr. 11, 2005. URL: http://www.awarix.com.
St. Vincent's is Digital Flagship D. Lockridge; Birmingham Medical News [Online] Sep. 2005.
Strom, Stephanie; "Old Pills Finding New Medicine Cabinets" NY Times, May 18, 2005.
Subnotebooks, Phones, and More. St. Vincent's Gets on Track. Mobile Health Data [Online], Nov. 19, 2004. URL:http://www.awarix.com.
"Two automatic identification technology, neither new in the sense if being recent developments . . . " Patient Safety & Quality Healthcare [Online] Aug. 2005_ URL: http://www_awarix.com.
Wisconsin Physicians Service (WPS) Insurance Corporation, "How to Read Your Explanation of Benefits Chart," Jun. 16, 2012.

(56) References Cited

OTHER PUBLICATIONS www.ncoil.org/news/DrugCards2.doc dated Apr. 2002.
Non-Final Office Action for U.S. Appl. No. 16/819,258 dated Sep. 4, 2020, 13 pages.
U.S. Appl. No. 14/229,043, filed Mar. 28, 2014, Pinsonneault.
U.S. Appl. No. 15/084,034, filed Mar. 29, 2016, Geone et al.
U.S. Appl. No. 15/085,166, filed Mar. 30, 2016, Kaye et al.
U.S. Appl. No. 16/180,915, filed Nov. 5, 2018, Pinsonneault.
Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.
Anonymous, Medic; On-line Goes In-House, Chain Store Age Executive, Jan. 1987, vol. 63. Issue 1. USA: onlv.
Anonymous, Pharmacy Industiy Leaders Launch Firm to Supply Real-Time Data. PR Newswire. Jul. 30, 2001. p. 1. York. NY. USA.
Anonymous, TechRx Announces Successful Beta Deployment of T-Rex. PR Newswire. May.
Final Office Action for U.S. Appl. No. 13/827,676 dated Jul. 13, 2015.
Final Office Action for U.S. Appl. No. 14/145,027 dated Nov. 19, 2015.
Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.
Non-Final Office Action for U.S. Appl. No. 12/388,956 dated Feb. 3, 2011.
Non-Final Office Action for U.S. Appl. No. 13/827,676 dated Dec. 26, 2014.
Non-final Office Action for U.S. Appl. No. 13/827,676 dated Dec. 30, 2015.
Non-Final Office Action for U.S. Appl. No. 14/145,027 dated Mar. 23, 2015.
Notice of Allowance for U.S. Appl. No. 12/388,956 dated Jun. 14, 2011.
Sampson, R.J., Taking Control of Health Care Costs, Best's Review—Life Health Insurance Edition, Nov. 1983, 84, Issue 7, USA; Abstract only.
Non-Final Office Action for U.S. Appl. No. 15/427,746 dated Oct. 18, 2018, 9 pages.
Final Office Action for U.S. Appl. No. 15/427,746 dated Apr. 15, 2019, 10 pages.
Advisory Action for U.S. Appl. No. 15/427,746 dated Jul. 2, 2019, 4 pages.
Notice of Allowance for U.S. Appl. No. 15/427,746 dated Jul. 31, 2019, 13 pages.
Notice of Allowance for U.S. Appl. No. 15/427,746 dated Dec. 4, 2019, 15 pages.
Non-Final Office Action for U.S. Appl. No. 15/137,371 dated May 29, 2018, 33 pages.
Final Office Action for U.S. Appl. No. 15/137,371 dated Nov. 28, 2018, 24 pages.
Advisory Action for U.S. Appl. No. 15/137,371 dated Feb. 25, 2019, 5 pages.
Notice of Allowance for U.S. Appl. No. 15/137,371 dated May 2, 2019, 30 pages.
Examiner's Answer for U.S. Appl. No. 14/145,027 dated Sep. 7, 2016, 28 pages.
PTAB Decision on Appeal for U.S. Appl. No. 14/145,027 mailed May 31, 2018, 12 pages.
PTAB Decision on Request for Rehearing for U.S. Appl. No. 14/145,027 mailed Aug. 30, 2018, 10 pages.
Advisory Action received for U.S. Appl. No. 15/085,166, dated Jan. 29, 2021, 5 pages, US.
U.S. Appl. No. 16/453,509, filed Jun. 26, 2019, Pending.
U.S. Notice of Allowance received for U.S. Appl. No. 16/819,258, dated Nov. 16, 2020, 8 pages, U.S.
Non-Final Office Action received for U.S. Appl. No. 16/551,962, dated Mar. 2, 2021, 38 pages.
Supplemental Notice of Allowability received for U.S. Appl. No. 16/180,915, dated Mar. 12, 2021, 11 pages.
Non-Final Office Action received for U.S. Appl. No. 15/085,166, dated Mar. 17, 2021, 12 pages.
Non-Final Office Action received for U.S. Appl. No. 16/453,509 dated Mar. 26, 2021, 45 pages.
United States Patent and Trademark Office, Notice of Allowance received for U.S. Appl. No. 15/085,166, dated Sep. 10, 2021, 21 pages, U.S.
United States Patent and Trademark Office, Corrected Notice of Allowability received for U.S. Appl. No. 15/085,166, dated Sep. 20, 2021, 6 pages, U.S.
Advisory Action for U.S. Appl. No. 14/193,294 dated Nov. 9, 2017, 3 pages.
Advisory Action for U.S. Appl. No. 15/085,166 dated Apr. 11, 2019, 4 pages.
Advisory Action for U.S. Appl. No. 15/085,166 dated Apr. 29, 2020, 3 pages.
Decision to Grant European Patent Application No. 13809457.8 dated May 18, 2017.
Extended European Search Report for European Application No. 13809457.8 dated Apr. 15, 2016, 6 pages.
Notice of Allowance and Fees(s) Due for U.S. Appl. No. 15/925,011 dated Jan. 22, 2021, 15 pages.
Office Action for U.S. Appl. No. 14/193,294 dated Sep. 19, 2018, 27 pages.
Office Action for U.S. Appl. No. 15/085,166 dated Jun. 29, 2018, 19 pages.
Office Action for U.S. Appl. No. 15/422,184 dated Aug. 27, 2019, 16 pages.
Office Action for U.S. Appl. No. 15/422,184 dated Feb. 15, 2019, 15 pages.
Office Action for U.S. Appl. No. 15/422,184 dated Jan. 14, 2020, 19 pages.
Office Action for U.S. Appl. No. 15/422,184 dated Sep. 10, 2018, 13 pages.
Office Action for U.S. Appl. No. 15/925,011 dated Jun. 27, 2019, 15 pages.
Office Action for U.S. Appl. No. 15/925,011 dated Oct. 24, 2019, 19 pages.
Office Action for U.S. Appl. No. 15/925,948 dated Jun. 25, 2019, 13 pages.
Office Action for U.S. Appl. No. 15/925,948 dated Oct. 23, 2019, 18 pages.
U.S. Appl. No. 17/012,565, "Method, Apparatus, and Computer Program Product for Performing an Alternative Evaluation Procedure in Response to an Electronic Message," Unpublished (filed Sep. 4, 2020), (Stacy Hopkins, et al., Inventors) (McKesson Corporation, Assignee), pending.
U.S. Appl. No. 17/092,705, "Computing System and Method for Automatically Reversing an Action Indicated by an Electronic Message," Unpublished (filed Nov. 9, 2020), (Patrick Harris, Inventor) (McKesson Corporation, Assignee), pending.
U.S. Appl. No. 16/792,413, "Method, Apparatus and Computer Program Product for Partitioning Prescription Transaction Costs in an Electronic Prescription Transaction," Unpublished (filed Feb. 17, 2020), (Jared Burdine, Inventor) (McKesson Corporation, Assignee), pending.
U.S. Appl. No. 16/867,286, "Method, Apparatus, and Computer Program Product for Constructing Electronic Message Responses Dependent Upon Historical Information," Unpublished (filed May 5, 2020), (Jared Burdine, et al., Inventor) (McKesson Corporation, Assignee), pending.
United States Patent and Trademark Office, Advisory Action for U.S. Appl. No. 15/422,184, dated Jun. 25, 2019, 4 pages, U.S.A.
United States Patent and Trademark Office, Advisory Action for U.S. Appl. No. 15/422,184, dated Mar. 26, 2020, 5 pages, U.S.A.
United States Patent and Trademark Office, Advisory Action for U.S. Appl. No. 15/925,011, dated Jan. 31, 2020, 3 pages, U.S.A.
United States Patent and Trademark Office, Advisory Action for U.S. Appl. No. 15/925,948, dated Jan. 31, 2020, 4 pages, U.S.A.

(56) References Cited

OTHER PUBLICATIONS

United States Patent and Trademark Office, Notice of Allowability received for U.S. Appl. No. 15/422,184, dated Nov. 16, 2020, 2 pages, U.S.A.
United States Patent and Trademark Office, Notice of Allowance received for U.S. Appl. No. 15/422,184, dated Oct. 13, 2020, 12 pages, U.S.A.
United States Patent and Trademark Office, Notice of Allowance received for U.S. Appl. No. 15/925,948, dated Nov. 5, 2020, 22 pages, U.S.A.
United States Patent and Trademark Office, Notice of Allowance received for U.S. Appl. No. 16/043,401, dated Aug. 10, 2020, 8 pages, U.S.A.
United States Patent and Trademark Office, Office Action for U.S. Appl. No. 15/925,011, dated Apr. 8, 2020, 17 pages, U.S.A.
United States Patent and Trademark Office, Office Action for U.S. Appl. No. 15/925,948, dated Mar. 23, 2020, 29 pages, U.S.A.
United States Patent and Trademark Office, Office Action received for U.S. Appl. No. 15/422,184, dated May 18, 2020, 31 pages, U.S.A.
United States Patent and Trademark Office, Office Action received for U.S. Appl. No. 15/925,011, dated Oct. 8, 2020, 8 pages, U.S.A.
CMS Updates Drug Dashboards with Prescription Drug Pricing and Spending Data, Data, Medicare Part D, Prescription drugs (Mar. 14, 2019).
How to Estimate the Cost of a Prescription. Pam Olson, Sr. Client Services Executive, Navitus Health Solutions (Year: 2015).
United States Patent and Trademark Office, Final Office Action received for U.S. Appl. No. 16/453,509, dated Aug. 18, 2021, 16 pages, U.S.
United States Patent and Trademark Office, Non-Final Office Action received for U.S. Appl. No. 16/792,413, dated Aug. 5, 2021, 32 pages, U.S.
United States Patent and Trademark Office, Non-Final Office Action received for U.S. Appl. No. 16/867,286, dated Feb. 22, 2022, 38 pages, U.S.
United States Patent and Trademark Office, Notice of Allowance received for U.S. Appl. No. 17/219,526, dated Feb. 3, 2022, 48 pages, U.S.
Zhu, V. et al., "Data for drugs available through low-cost prescription drug programs are available through pharmacy benefit manager and claims data," BMC Clinical Pharmacology, Jun. 22, 2012, vol. 12, No. 12., BioMed Central Ltd., UK.
Google NPL (non-patent literature) Search on "pharmacy payment benefit copay NDC database", retrieved from the Internet at <https//scholar.google.com/scholar?hl=en&as_sdt-3,47&g-pharmacy+payment+benefit+copay+NDC+database> on Feb. 20, 2022 at 3:02 pm, 1 page.
Google NPL (non-patent literature) Search on "pharmacy payment benefit copay NDC database", retrieved from the Internet at <https://www.google.com/search?g=pharmacy+payment+benefit+copay+ndc+database&source=int&tbs=cdr%3A1%2Ccd_min%3A1%2F1%2F2010%2 . . . > on Feb. 20, 2022 at 3:00 pm, 2 pages.
United States Patent and Trademark Office, Advisory Action received for U.S. Appl. No. 16/792,413, dated Mar. 10, 2022, 4 pages, US.
United States Patent and Trademark Office, Notice of Allowance and Fee(s) Due received for U.S. Appl. No. 17/219,526, dated Mar. 22, 2022, 11 pages, US.
United States Patent and Trademark Office, Notice of Allowance and Fee(s) Due received for U.S. Appl. No. 16/551,962, dated Mar. 16, 2022, 10 pages, US.
United States Patent and Trademark Office, Notice of Allowance and Fee(s) Due received for U.S. Appl. No. 17/092,705, dated Mar. 24, 2022, 9 pages, US.
United States Patent and Trademark Office, Notice of Allowance and Fee(s) Due received for U.S. Appl. No. 16/551,962, dated Mar. 1, 2022, 14 pages, US.
Scientific and Technical Information Center, Report of Information from Dialog (NPL (non-patent literature) Search Results, Abstracts only), dated Nov. 1, 2021, (Year: 2021), 9 pages.
United States Patent and Trademark Office, Advisory Action received for U.S. Appl. No. 16/453,509, dated Oct. 12, 2021, 5 pages, U.S.
United States Patent and Trademark Office, Final Office Action received for U.S. Appl. No. 16/551,962, dated Nov. 4, 2021, 32 pages, U.S.
United States Patent and Trademark Office, Non-Final Office Action received for U.S. Appl. No. 17/012,565, dated Apr. 12, 2022, 19 pages, U.S.A.
United States Patent and Trademark Office, Non-Final Office Action received for U.S. Appl. No. 16/453,509, dated Apr. 28, 2022, 16 pages, U.S.A.
United States Patent and Trademark Office, Non-Final Office Action received for U.S. Appl. No. 16/552,021, dated May 3, 2022, 60 pages, U.S.A.
United States Patent and Trademark Office, Non-Final Office Action received for U.S. Appl. No. 17/175,939, dated May 12, 2022, 48 pages, U.S.A.
United States Patent and Trademark Office, Notice of Allowance received for U.S. Appl. No. 17/092,705, dated Dec. 23, 2021, 42 pages, U.S.
United States Patent and Trademark Office, Non-Final Office Action received for U.S. Appl. No. 15/085,166, dated Jan. 10, 2022, 12 pages, U.S.
United States Patent and Trademark Office, Final Office Action received for U.S. Appl. No. 16/792,413, dated Jan. 10, 2022, 80 pages, U.S.
Dubois, Robert W., "Rx Drug Costs: List Prices Versus Net Prices And The Importance Of Staying Within The Data", Health Affairs Blog, Mar. 2019, 7 pages.
Kamal, Rabah, et al., "What are the recent and forecasted trends in prescription drug spending?" Peterson—KFF Health System Tracker, Feb. 20, 2019, 19 pages, Peterson Center on Healthcare.
Cepeda, Maria Soledad, et al., "Quantification of missing prescriptions in commercial claims databases : results of a cohort study.", Pharmacoepidemiology and Drug Safety, Apr. 2017, pp. 386-392, vol. 26, Epub Jan. 25, 2017 on Wiley Online Library.
United States Patent and Trademark Office, Final Office Action received for U.S. Appl. No. 16/867,286, dated Sep. 8, 2022, 19 pages, U.S.
United States Patent and Trademark Office, Notice of Allowance received for U.S. Appl. No. 16/792,413, dated Sep. 8, 2022, 18 pages, U.S.
United States Patent and Trademark Office, Notice of Allowance received for U.S. Appl. No. 17/012,565, dated Sep. 21, 2022, 11 pages, U.S.
United States Patent and Trademark Office, Notice of Allowance received for U.S. Appl. No. 16/453,509, dated Oct. 3, 2022, 23 pages, U.S.
United States Patent and Trademark Office, Final Office Action received for U.S. Appl. No. 17/175,939, dated Oct. 5, 2022, 30 pages, U.S.
United States Patent and Trademark Office, Nonfinal Office Action received for U.S. Appl. No. 17/162,461, dated Oct. 5, 2022, 47 pages, U.S.
United States Patent and Trademark Office, Nonfinal Office Action received for U.S. Appl. No. 17/158,118, dated Oct. 7, 2022, 46 pages, U.S.
United States Patent and Trademark Office, Notice of Allowance received for U.S. Appl. No. 15/085,166, dated Jun. 15, 2022, 18 pages, U.S.
United States Patent and Trademark Office, Final Office Action received for U.S. Appl. No. 17/012,565, dated Jul. 25, 2022, 43 pages, U.S.
Chu, Kuan-Yu, et al., "Incremental analysis of the reengineering of an outpatient billing process: an empirical study in a public hospital", BMC Health Services Research, Jun. 13, 2013, vol. 13, No. 215, 8 pages, BioMed Central Ltd, UK.
Google Patents Search (including Web Search History, Prior Art Search Printable History Generator) on "pharmacy payment benefit copay NDC database) (prescription) (code) (refills) (error code) country:US before:filing:Dec. 31, 2013", retrieved from the Internet at <https://patents.google.com/?q=pharmacy+payment+benefit+

(56) References Cited

OTHER PUBLICATIONS copay+NDC+database&q=prescription&q=code&q=refills&q=error+code&country=US&before=filing:20131231> retrieved on Jun. 1, 2022, 4 pages.
Google Scholar Search (including Web Search History, Prior Art Search Printable History Generator) on "pharmacy payment benefit copay NDC database prescription . . . ", retrieved from the Internet at <https://scholar.google.com/scholar?hl=en&as_sdt-0%2C47&as_ylo-2010&as_yhi=2013&q=pharmacy+payment+benefit+copay+NDC+database+pres . . . > retrieved on Jun. 1, 2022, 3 pages.
United States Patent and Trademark Office, Non-Final Office Action received for U.S. Appl. No. 16/792,413, dated May 24, 2022, 48 pages, US.
United States Patent and Trademark Office, Non-Final Office Action received for U.S. Appl. No. 17/144,426, dated May 31, 2022, 42 pages, US.
United States Patent and Trademark Office, Notice of Allowance received for U.S. Appl. No. 17/092,705, dated May 31, 2022, 9 pages, US.
United States Patent and Trademark Office, Notice of Allowance received for U.S. Appl. No. 17/219,526, dated Jun. 2, 2022, 8 pages, US.
United States Patent and Trademark Office, Notice of Allowance received for U.S. Appl. No. 16/551,962, dated Jun. 8, 2022, 11 pages, US.
United States Patent and Trademark Office, Notice of Allowance received for U.S. Appl. No. 16/552,021, dated Oct. 20, 2022, 14 pages, US.
Hsee, Christopher K., et al., "General Evaluability Theory", Perspectives on Psychological Science, Jul. 2010, pp. 343-355, vol. 5, No. 4, Sage Publications, Inc. on behalf of the Association for Psychological Science retrieved from the Internet at <URL: https://www.jstor.org/stable/41613442>.
United States Patent and Trademark Office, Advisory Action received for U.S. Appl. No. 16/867,286, dated Dec. 6, 2022, 8 pages, US.
United States Patent and Trademark Office, Advisory Action received for U.S. Appl. No. 17/175,939, dated Dec. 22, 2022, 5 pages, US.
United States Patent and Trademark Office, Final Office Action received for U.S. Appl. No. 17/144,426, dated Dec. 8, 2022, 21 pages, US.
United States Patent and Trademark Office, Advisory Action received for U.S. Appl. No. 16/867,286, dated Feb. 6, 2023, 3 pages, US.
United States Patent and Trademark Office, Advisory Action received for U.S. Appl. No. 17/144,426, dated Mar. 3, 2023, 6 pages, US.
United States Patent and Trademark Office, Final Office Action received for U.S. Appl. No. 17/158,118, dated Mar. 3, 2023, 19 pages, US.

\* cited by examiner

METHOD, APPARATUS, AND COMPUTER PROGRAM PRODUCT FOR PROVIDING ESTIMATED PRESCRIPTION COSTS

CROSS REFERENCE TO RELATED APPLICATION

This application is a continuation-in-part of and claims priority to U.S. application Ser. No. 16/453,509, filed Jun. 26, 2019, the entire contents of which are hereby incorporated by reference.

TECHNOLOGICAL FIELD

Embodiments of the present invention relate generally to healthcare transactions and, more particularly, to methods, apparatuses, and computer program products for providing estimated costs and targeted out-of-pocket costs for prescribed medication.

BACKGROUND

In the healthcare services industry, physicians and other prescribers may not always have accurate information available to them during service regarding costs of medication. Providing the costs of such prescriptions to prescribers during the service can be a challenge with today's healthcare provider systems as benefit coverage inquiries continue to evolve. Over time, the financial structures for prescription claims have become more sophisticated (i.e. formulary tiers, deductibles, maximum benefits, etc.), and prices can vary greatly between pharmacies. Patients that are not aware of the cost of their prescribed medication may be less likely to adhere to the prescribed regimen, as they may choose not to purchase the prescription when they visit the pharmacy and learn the cost.

BRIEF SUMMARY

Methods, apparatuses, and computer program products are therefore provided for supplying a prescriber at the point of prescribing (e.g., during a healthcare service with a patient) with information to provide to a patient, and particularly for providing estimated prescription costs and/or targeted out-of-pockets costs in the event of an insufficient or absent response from a benefits manager. Other attempts at providing pricing information at the prescriber during a service may involve inquiring and obtaining a response from a patient's benefits manager (e.g. insurance company and/or payor) to provide the patient with accurate information concerning prescription costs and out-of-pocket expenses prior to visiting a pharmacy. However, problems may arise when a response from the pharmacy benefits manager is lacking certain required information, or, in some instances, when a response is not provided, or not provided within a specified time period.

A computer-implemented method is provided, including receiving, by one or more service provider computers comprising one or more processors and from a prescriber computer, a prescription benefit coverage inquiry associated with a patient and a prescribed medication. The method further includes transmitting, by the one or more service provider computers, the prescription benefit coverage inquiry to a pharmacy claims processor computer for processing. In an instance in which a response from the pharmacy claims processor computer is not received or a received response fails to satisfy a predefined condition, the method may include (a) determining, with a processor and based on historical data comprising prior prescription transactions associated with the prescribed medication, an estimated cost range for the prescribed medication, (b) determining whether an incentive is available based on the prescription benefit coverage inquiry, (c) in an instance the incentive is available, determining a targeted out-of-pocket cost and providing the targeted out-of-pocket cost to the prescriber computer, and (d) providing the estimated cost range for the prescribed medication to the prescriber computer.

In certain embodiments, the method may include determining the prescription benefit coverage inquiry reflects a government plan, and in response thereto, determining the prescription benefit coverage inquiry is not eligible for an incentive. In an instance the incentive is available, the method may further include generating an incentive notification message, and transmitting the incentive notification message to the prescriber computer. The incentive notification message may include a notification that an incentive may be available.

The method may further include determining whether the incentive is available by receiving an indication of a medication identifier associated with the prescribed medication, and comparing the medication identifier to a list of medication identifiers representing medications for which an incentive is available to determine whether a match exists. In an instance it is determined the match exists, the method includes determining the incentive is available. In an instance it is determined the match does not exist, the method includes determining the incentive is not available. In an instance the incentive is available, the method may include determining whether the prescription benefit coverage inquiry qualifies for the incentive.

In certain embodiments, determining the estimated cost range comprises determining an average value based on a paid amount associated with each of the prescription transactions in the historical data, identifying a subset of prescription transactions from the historical data based on the average value, and from the subset of prescription transactions, determining the estimated cost range of the prescribed medication that ranges a calculated amount from the average value.

In certain embodiments, identifying a subset of prescription transactions from the historical data based on the average value comprises comparing each paid amount to a calculated amount associated with the average value to determine one or more paid amounts that are within a predefined range of the calculated amount, and including, based on the comparison, transactions comprising paid amounts within the predefined range of the calculated amount in the subset of prescription transactions.

According to certain embodiments, providing the estimated cost range and the targeted out-of-pocket cost for the prescribed medication to the prescriber computer relative to receiving a prescription benefit coverage inquiry associated with a patient and a prescribed medication is performed in real-time or near real-time.

An apparatus is provided, comprising at least one processor and at least on memory including computer program code, the at least one memory and the computer program code configured to, with the processor, cause the apparatus to at least receive, by one or more service provider computers comprising one or more processors and from a prescriber computer, a prescription benefit coverage inquiry associated with a patient and a prescribed medication. The at least one memory and the computer program code configured to, with the processor, cause the apparatus to transmit, by the one or more service provider computers, the prescription benefit coverage inquiry to a pharmacy claims processor computer for processing.

In an instance in which a response from the pharmacy claims processor computer is not received or a received response fails to satisfy a predefined condition, the at least one memory and the computer program code configured to, with the processor, cause the apparatus to (a) determine, based on historical data comprising prior prescription transactions associated with the prescribed medication, an estimated cost range for the prescribed medication, (b) determine whether an incentive is available based on the prescription benefit coverage inquiry, (c) in an instance the incentive is available, determine a targeted out-of-pocket cost and provide the targeted out-of-pocket cost to the prescriber computer, and (d) provide the estimated cost range for the prescribed medication to the prescriber computer.

In certain embodiments, the at least one memory and the computer program code are further configured to cause the apparatus to may determine the prescription benefit coverage inquiry reflects a government plan, and in response thereto, determine the prescription benefit coverage inquiry is not eligible for an incentive. In certain embodiments, in an instance the incentive is available, the at least one memory and the computer program code are further configured to cause the apparatus to at least generate an incentive notification message, wherein the incentive notification message comprises a notification that an incentive may be available and transmit the incentive notification message to the prescriber computer. In certain embodiments, determining whether the incentive is available comprises receiving an indication of a medication identifier associated with the prescribed medication, and comparing the medication identifier to a list of medication identifiers representing medications for which an incentive is available to determine whether a match exists.

In an instance it is determined the match exists, the at least one memory and the computer program code are further configured to cause the apparatus to determine the incentive is available. In an instance it is determined the match does not exist, the at least one memory and the computer program code are further configured to cause the apparatus to determine the incentive is not available. In an instance the incentive is available, the at least one memory and the computer program code are further configured to cause the apparatus to at least determine whether the prescription benefit coverage inquiry qualifies for the incentive.

A computer program product is also provided. The computer program product may include at least one non-transitory computer-readable storage medium having computer-executable program code instructions stored therein, the computer-executable program code instructions comprising program code instructions to receive, by one or more service provider computers comprising one or more processors and from a prescriber computer, a prescription benefit coverage inquiry associated with a patient and a prescribed medication. The computer-executable program code instructions may include program code instructions to transmit, by the one or more service provider computers, the prescription benefit coverage inquiry to a pharmacy claims processor computer for processing. In an instance in which a response from the pharmacy claims processor computer is not received or a received response fails to satisfy a predefined condition, the computer-executable program code instructions may further include program code instructions to (a) determine, based on historical data comprising prior prescription transactions associated with the prescribed medication, an estimated cost range for the prescribed medication, (b) determine whether an incentive is available based on the prescription benefit coverage inquiry, and (c) in an instance the incentive is available, determine a targeted out-of-pocket cost and providing the targeted out-of-pocket cost to the prescriber computer, and (d) provide the estimated cost range for the prescribed medication to the prescriber computer.

In certain embodiments, the computer-executable program code instructions may further include program code instructions to cause the apparatus to determine the prescription benefit coverage inquiry reflects a government plan, and in response thereto, determine the prescription benefit coverage inquiry is not eligible for an incentive.

In an instance the incentive is available, the computer-executable program code instructions may further include program code instructions to generate an incentive notification message and transmit the incentive notification message to the prescriber computer.

In certain embodiments, determining whether the incentive is available comprises receiving an indication of a medication identifier associated with the prescribed medication, and comparing the medication identifier to a list of medication identifiers representing medications for which an incentive is available to determine whether a match exists. In an instance it is determined the match exists, the computer-executable program code instructions may further include program code instructions to cause the apparatus to determine the incentive is available. In an instance it is determined the match does not exist, the computer-executable program code instructions may further include program code instructions to determine the incentive is not available. In an instance the incentive is available, the computer-executable program code instructions may further include program code instructions to at least determine whether the prescription benefit coverage inquiry qualifies for the incentive.

An apparatus is provided, with means for receiving, by one or more service provider computers comprising one or more processors and from a prescriber computer, a prescription benefit coverage inquiry associated with a patient and a prescribed medication. The apparatus further includes means for transmitting, by the one or more service provider computers, the prescription benefit coverage inquiry to a pharmacy claims processor computer for processing. In an instance in which a response from the pharmacy claims processor computer is not received or a received response fails to satisfy a predefined condition, the apparatus may include (a) means for determining, based on historical data comprising prior prescription transactions associated with the prescribed medication, an estimated cost range for the prescribed medication, (b) means for determining whether an incentive is available based on the prescription benefit coverage inquiry, (c) in an instance the incentive is available, means for determining a targeted out-of-pocket cost and providing the targeted out-of-pocket cost to the prescriber computer, and (d) means for providing the estimated cost range for the prescribed medication to the prescriber computer.

The above summary is provided merely for purposes of summarizing some example embodiments of the invention so as to provide a basic understanding of some aspects of the invention. Accordingly, it will be appreciated that the above described example embodiments are merely examples and should not be construed to narrow the scope or spirit of the disclosure in any way. It will be appreciated that the scope of the disclosure encompasses many potential embodiments, some of which will be further described below, in addition to those here summarized.

BRIEF DESCRIPTION OF THE SEVERAL VIEWS OF THE DRAWINGS

Figure 1:
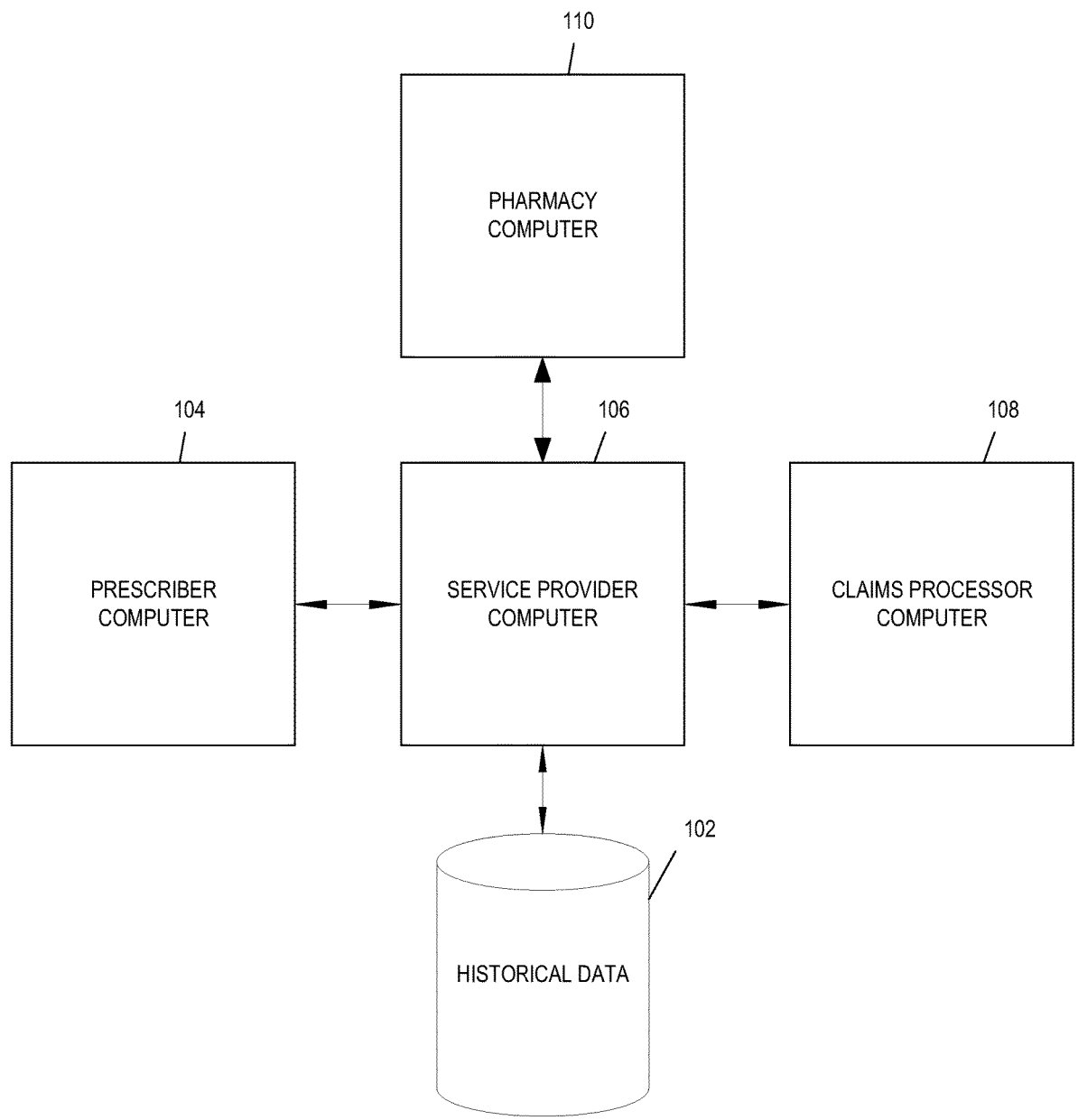
Figure 2:
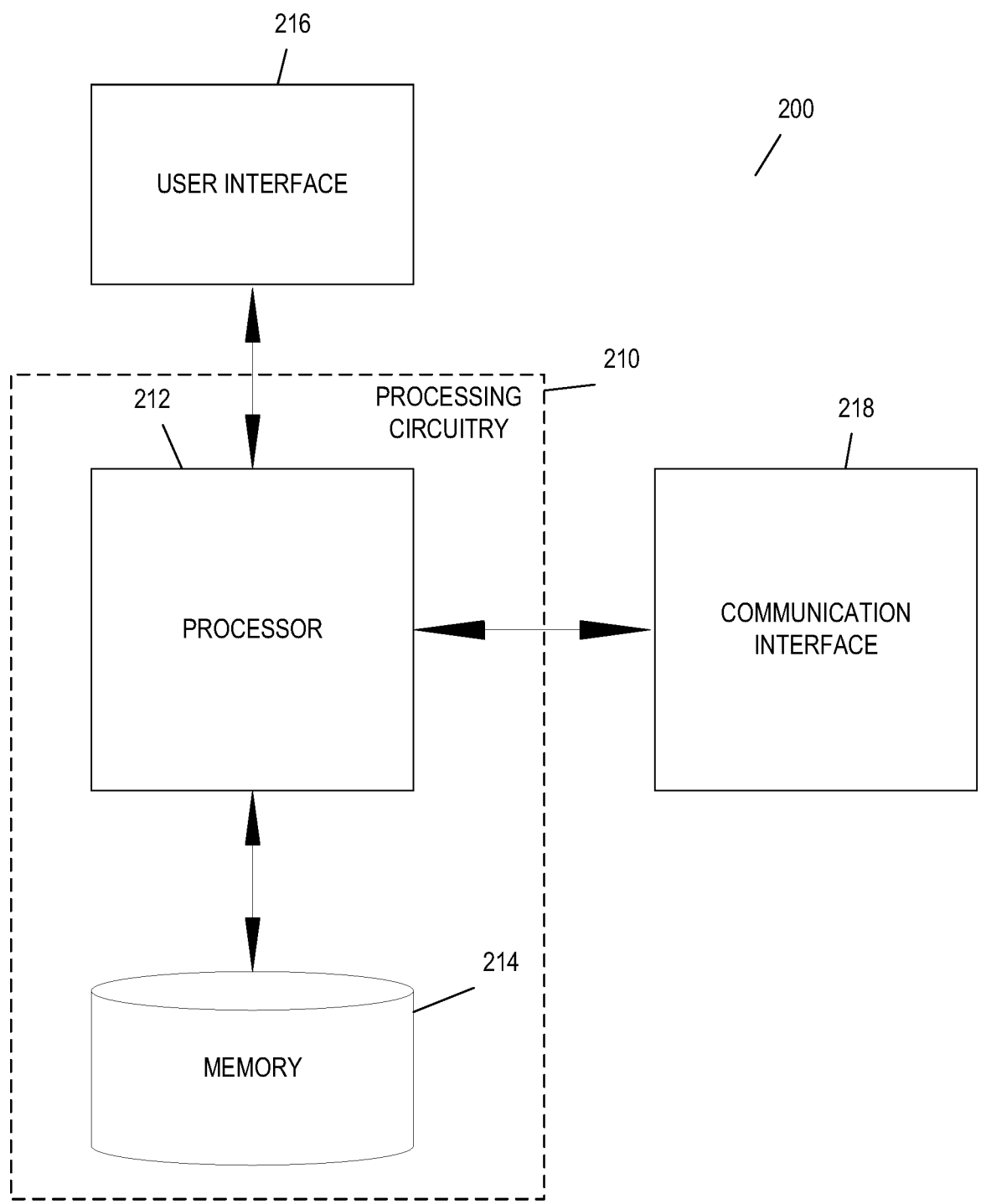
Figure 3:
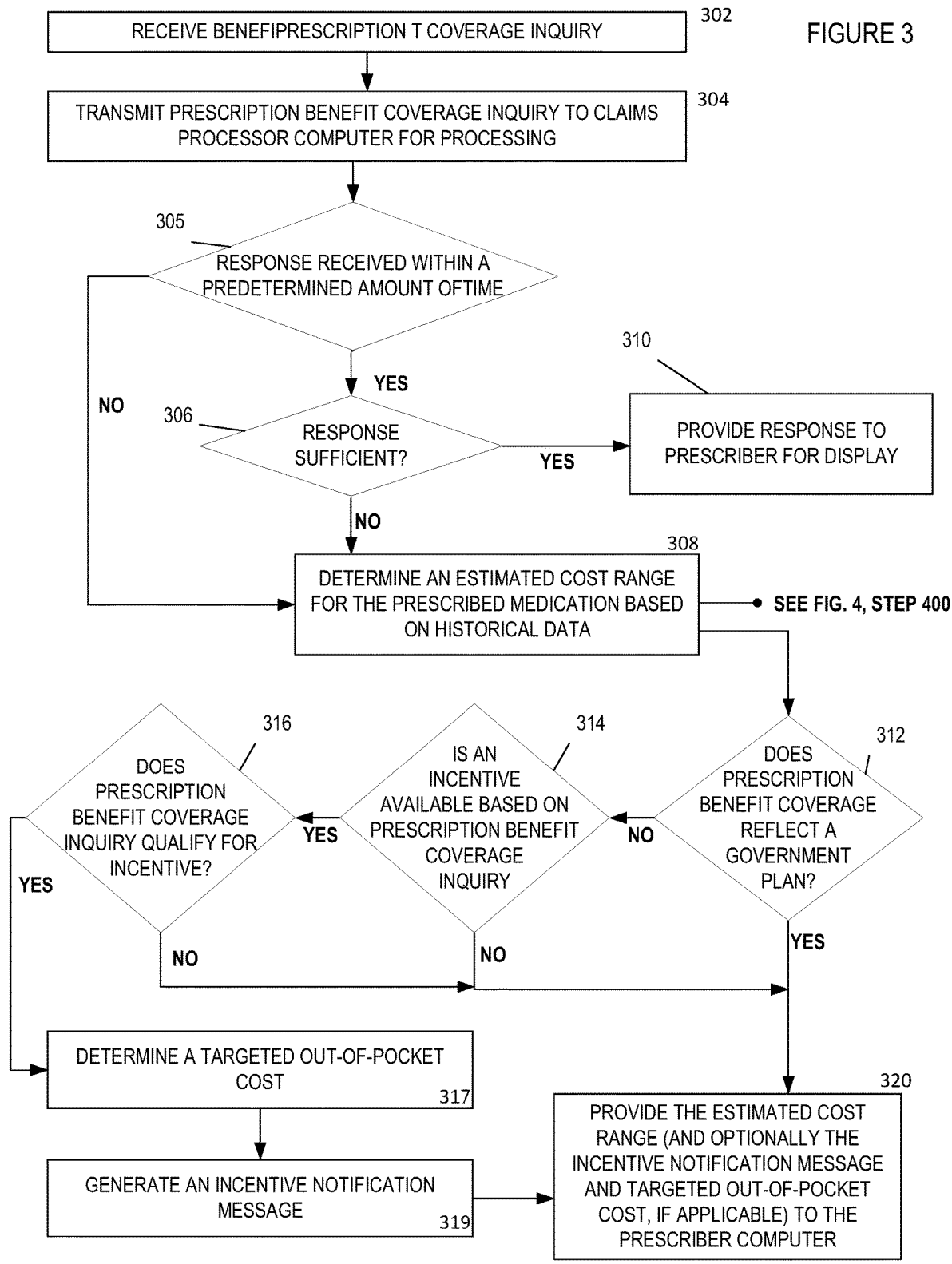
Figure 4:
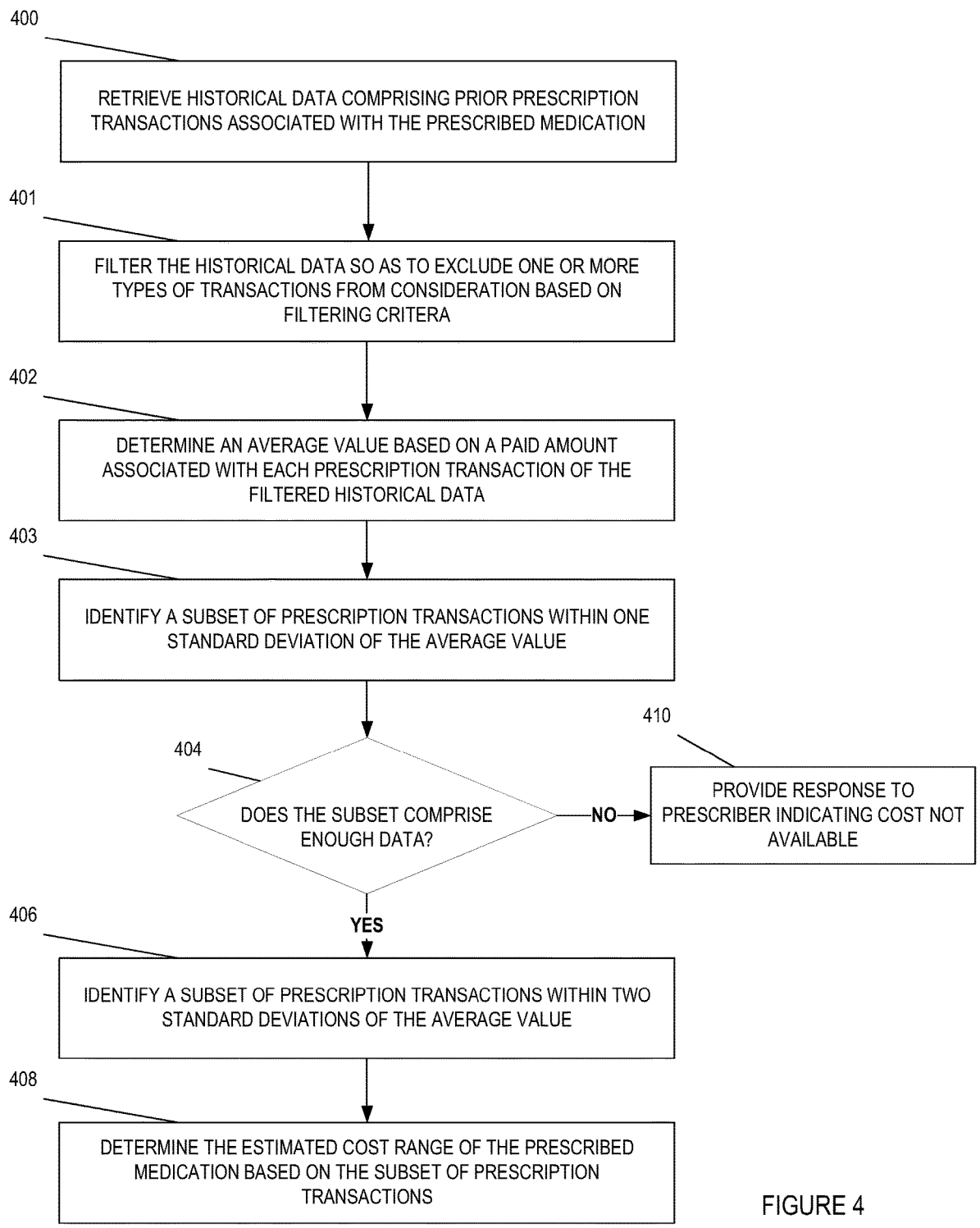

Having thus described embodiments of the invention in general terms, reference will now be made to the accompanying drawings, which are not necessarily drawn to scale, and wherein:

FIG. 1 is an example overview of a system that can be used to practice some example embodiments described herein;

FIG. 2 is an exemplary schematic diagram of an apparatus in accordance with some example embodiments; and FIGS. 3-4 are flowcharts of operations that may be performed in accordance with some example embodiments.

DETAILED DESCRIPTION

Some embodiments of the present invention will now be described more fully hereinafter with reference to the accompanying drawings, in which some, but not all embodiments of the invention are shown. Indeed, various embodiments of the invention may be embodied in many different forms and should not be construed as limited to the embodiments set forth herein; rather, these embodiments are provided so that this disclosure will satisfy applicable legal requirements. Like reference numerals refer to like elements throughout.

As used herein, where a computing device is described herein to receive data from another computing device, it will be appreciated that the data may be received directly from the other computing device and/or may be received indirectly via one or more intermediary computing devices, such as, for example, one or more servers, relays, routers, network access points, and/or the like. Similarly, where a computing device is described herein to transmit data to other computing device, it will be appreciated that the data may be sent directly to the other computing device or may be sent to the other computing device via one or more interlinking computing devices, such as, for example, one or more servers, relays, routers, network access points, and/or the like.

FIG. 1 is an overview of a system that can be used to analyze prescription transactions and provide estimated cost ranges, and/or targeted out-of-pocket costs of prescriptions according to certain example embodiments described herein. The prescriber computer 104 may be associated with a healthcare provider, such as an entity that may prescribe medication and/or treatments, for example, a physician's office, clinic, long-term care facility, hospital, etc. While the exemplary prescriber computer 104 may be frequently referenced herein as part of a physician's office or healthcare network, the prescriber computer 104 may be associated with any other healthcare provider, such as a hospital, urgent care center, dentist, and/or other medical facility.

The prescriber computer 104 may be any processor-driven device that facilitates the processing of prescription benefit coverage inquiries made by physicians or clinical staff, and the communication of information associated with prescription benefit coverage inquiries to the service provider computer 106. The execution of the computer-implemented instructions by the prescriber computer 104 and/or service provider computer 106 may form a special purpose computer or other particular machine that is operable to facilitate the processing of prescription benefit coverage inquiries made by physicians, doctors, clinical staff, pharmacists, and/or the like, and the communication of information associated therewith to a service provider computer and/or claims processor computer 108.

The service provider computer 106 may include, but is not limited to, a processor-driven device that is configured for receiving, processing, and fulfilling inquiries, responses, and/or requests from the prescriber computer 104 and/or the claims processor computer 108 (described below), relating to prescription benefit coverage inquiries, prescription tracking, claims processing, benefits, billing, other healthcare transactions, and/or other related activities. Additionally or alternatively, the service provider computer 106 may be operable to facilitate the receipt, routing, and/or processing of prescription benefit coverage inquiries and/or associated responses amongst various components and/or subsystems such as, but not limited to, those depicted in FIG. 1.

In certain exemplary embodiments, the service provider computer 106 may be configured as or may comprise a switch or router that evaluates, processes, modifies, reformats, generates, and/or routes prescription benefit coverage inquiries and/or other healthcare transactions. For example, the service provider computer 106 may route prescription benefit coverage inquiries communicated from the prescriber computer 104 to a claims processor computer 108, such as that associated with a pharmacy benefits manager (PBM), an insurer, a Medicare or other government healthcare insurance program payor, or other payor.

Additionally or alternatively, the service provider computer 106 may reformat prescription benefit coverage inquiries into another form of transaction and modify the recipient information of the reformatted transaction before routing the reformatted transaction to another party, such as a claims processor computer 108. The service provider computer 106 may also direct a prescription benefit coverage inquiry to a claims processor computer 108, which may in turn route a response to the service provider computer 106. The service provider computer 106 may then direct the response to the prescriber computer 104 or other associated entity.

In addition to receiving and storing information, the service provider computer 106 may be further operable to access and/or be in communication with one or more suitable data storage devices, such as a database 102, for storing historical data and/or other various data. In some embodiments, the database 102 comprises data relating to prescription transactions associated with one or more pharmacy computers 110. Data, such as for example, historical data, may be provided by and/or stored in database 102 by a number of entities which may comprise the prescriber computer 104, service provider computer 106, claims processor computer 108, one or more pharmacy computers 110 and/or other related entities. In certain embodiments, data is provided to database 102 by one or more pharmacy computers 110 associated with one or more pharmacies. These one or more pharmacy computers 110 may voluntarily provide data to database 102 (and/or service provider computer 106, which may in turn store the historical data on database 102), such as historical data related to prior prescription transactions that have taken place at each respective pharmacy. In this regard, the historical data may comprise paid amounts by consumers (e.g., patients) at particular pharmacies for particular prescriptions, and may reflect cash prices (without any insurance payment or coverage), and/or may reflect paid amounts by the consumer given a paid and/or adjudicated prescription claim by the claims processor computer 108. In an embodiment, the one or more pharmacies may be taking part in a program wherein certain data is supplied to database 102 by the one or more pharmacy computers 110 associated with the one or more pharmacies in an effort to provide patients and prescribers with accurate cost information at a point of prescribing. According to some embodiments, the historical data may indicate other characteristics about respective prescription transactions, such as the state or other location information of the dispensing pharmacy, the dispense date, information regarding preauthorization requirements, and/or the like. The service provider computer 106 may be configured to mine and store pertinent information from any healthcare transactions and/or claims received and/or generated by the service provider computer 106, particularly data that may utilized by example embodiments described herein to estimate cost ranges of prescriptions.

The service provider computer 106 may transmit responses regarding the prescription benefit coverage inquires to the prescriber computer 104. For example, the service provider computer 106 may notify the prescriber computer 104 of and/or provide a response related to a prescription benefit coverage inquiry from the claims processor computer 108, such as the amount the patient should expect to pay for the prescription at a given pharmacy. However, according to some example embodiments, a response from the claims processor computer 108 may not be received, and the service provider computer 106 may provide a cost estimate of a prescription, as described in further detail below. The service provider computer 106 may be further configured to provide a targeted out-of-pocket cost based on an incentive from a drug manufacturer. In this regard, a message or other notification may be appended to or included in the response transmitted to the prescriber computer 104.

The example system of FIG. 1 described above is provided merely as an example and it will be appreciated that the example embodiments provided herein may be implemented as or employed by any number of system architectures. Some modifications may be made to certain embodiments. It will be further appreciated that any of the components of FIG. 1 are configured to communicate over a network, or network(s), as described in further detail herein.

Referring now to FIG. 2, apparatus 200 is a computing device(s) configured for implementing a prescriber computer 104, service provider computer 106, pharmacy computer 110, and/or claims processor computer 108, according to example embodiments.

Apparatus 200 may at least partially or wholly embody any of the prescriber computer 104, service provider computer 106, pharmacy computer 110, and/or claims processor computer 108. Apparatus 200 may therefore implement any of the prescriber computer 104, service provider computer 106, pharmacy computer 110, and/or claims processor computer 108, in accordance with some example embodiments, or may be implemented as a distributed system that includes any of the prescriber computer 104, service provider computer 106, pharmacy computer 110, claims processor computer 108, and/or associated network(s).

It should be noted that the components, devices, and elements illustrated in and described with respect to FIG. 2 may not be mandatory and thus some may be omitted in certain embodiments. For example, FIG. 2 illustrates a user interface 216, as described in more detail below, which may be optional in any of the prescriber computer 104, service provider computer 106, pharmacy computer 110, and/or claims processor computer 108. Additionally, some embodiments may include further or different components, devices, or elements beyond those illustrated in and described with respect to FIG. 2.

Continuing with FIG. 2, processing circuitry 210 may be configured to perform actions in accordance with one or more example embodiments disclosed herein. In this regard, the processing circuitry 210 may be configured to perform and/or control performance of one or more functionalities of apparatus 200 in accordance with various example embodiments. The processing circuitry 210 may be configured to perform data processing, application execution, and/or other processing and management services according to one or more example embodiments. In some embodiments apparatus 200, or a portion(s) or component(s) thereof, such as the processing circuitry 210, may be embodied as or comprise a circuit chip. The circuit chip may constitute means for performing one or more operations for providing the functionalities described herein.

In some example embodiments, the processing circuitry 210 may include a processor 212, and in some embodiments, such as that illustrated in FIG. 2, may further include memory 214. The processing circuitry 210 may be in communication with or otherwise control a user interface 216, and/or a communication interface 218. As such, the processing circuitry 210, such as that included in any of the prescriber computer 104, service provider computer 106, pharmacy computer 110, claims processor computer 108, and/or apparatus 200 may be embodied as a circuit chip (e.g., an integrated circuit chip) configured (e.g., with hardware, software, or a combination of hardware and software) to perform operations described herein.

The processor 212 may be embodied in a number of different ways. For example, the processor 212 may be embodied as various processing means such as one or more of a microprocessor or other processing element, a coprocessor, a controller, or various other computing or processing devices including integrated circuits such as, for example, an ASIC (application specific integrated circuit), an FPGA (field programmable gate array), or the like. Although illustrated as a single processor, it will be appreciated that the processor 212 may comprise a plurality of processors. The plurality of processors may be in operative communication with each other and may be collectively configured to perform one or more functionalities of apparatus 200 as described herein. The plurality of processors may be embodied on a single computing device or distributed across a plurality of computing devices collectively configured to function as prescriber computer 104, service provider computer 106, pharmacy computer 110, claims processor computer 108, and/or apparatus 200. In some example embodiments, the processor 212 may be configured to execute instructions stored in the memory 214 or otherwise accessible to the processor 212. As such, whether configured by hardware or by a combination of hardware and software, the processor 212 may represent an entity (e.g., physically embodied in circuitry—in the form of processing circuitry 210) capable of performing operations according to embodiments of the present invention while configured accordingly. Thus, for example, when the processor 212 is embodied as an ASIC, FPGA, or the like, the processor 212 may be specifically configured hardware for conducting the operations described herein. Alternatively, as another example, when the processor 212 is embodied as an executor of software instructions, the instructions may specifically configure the processor 212 to perform one or more operations described herein.

In some example embodiments, the memory 214 may include one or more non-transitory memory devices such as, for example, volatile and/or non-volatile memory that may be either fixed or removable. In this regard, the memory 214 may comprise a non-transitory computer-readable storage medium. It will be appreciated that while the memory 214 is illustrated as a single memory, the memory 214 may comprise a plurality of memories. The plurality of memories may be embodied on a single computing device or may be distributed across a plurality of computing devices. The memory 214 may be configured to store information, data, applications, computer program code, instructions and/or the like for enabling apparatus 200 to carry out various functions in accordance with one or more example embodiments. For example, when apparatus 200 is implemented as service provider computer 106, memory 214 may be configured to store computer program code for performing corresponding functions thereof, as described herein according to example embodiments.

Still further, memory 214 may be configured to store routing tables, that facilitate determining the destination of communications received from a prescriber computer 104, and/or claims processor computer 108. Memory 214 may further include reconciliation tables for tracking the prescription benefit coverage inquiries received from the prescriber computer 104, and reconciling them with responses received from claims processor computer 108. The memory 214 may be modified as described herein, to store reformatted prescription benefit coverage inquiries with additional information received, determined and/or generated according to example embodiments.

The memory 214 may be further configured to buffer input data for processing by the processor 212. Additionally or alternatively, the memory 214 may be configured to store instructions for execution by the processor 212. In some embodiments, the memory 214 may include one or more databases, such as database 102, that may store a variety of files, contents, or data sets, such as but not limited to historical data. Among the contents of the memory 214, applications may be stored for execution by the processor 212 to carry out the functionality associated with each respective application. In some cases, the memory 214 may be in communication with one or more of the processor 212, user interface 216, and/or communication interface 218, for passing information among components of apparatus 200.

The optional user interface 216 may be in communication with the processing circuitry 210 to receive an indication of a user input at the user interface 216 and/or to provide an audible, visual, mechanical, or other output to the user. As such, the user interface 216 may include, for example, a keyboard, a mouse, a display, a touch screen display, a microphone, a speaker, and/or other input/output mechanisms. As such, in embodiments in which apparatus 200 implemented as the prescriber computer 104, the user interface 216 may, in some example embodiments, provide means for user entry of insurance information, patient information, details relating to a prescription, and/or the like, and for provision of information relating to the estimated cost of a prescription, as described in further detail below. The user interface 216 may further enable obtaining patient consent for a benefit inquiry to occur according to example embodiments. In some example embodiments, aspects of user interface 216 may be limited or the user interface 216 may not be present.

The communication interface 218 may include one or more interface mechanisms for enabling communication with other devices and/or networks. In some cases, the communication interface 218 may be any means such as a device or circuitry embodied in either hardware, or a combination of hardware and software that is configured to receive and/or transmit data from/to a network and/or any other device or module in communication with the processing circuitry 210. By way of example, the communication interface 218 may be configured to enable communication amongst any of prescriber computer 104, service provider computer 106, pharmacy computer 110, claims processor computer 108, and/or apparatus 200 over a network, and/or to format an electronic healthcare transaction and/or benefit inquiry. Accordingly, the communication interface 218 may, for example, include supporting hardware and/or software for enabling wireless and/or wireline communications via cable, digital subscriber line (DSL), universal serial bus (USB), Ethernet, or other methods.

The network, such as the network in which the system of FIG. 1 or components thereof or components described herein may operate, (e.g., prescriber computer 104, service provider computer 106, pharmacy computer 110, claims processor computer 108, and/or apparatus 200, and/or the like) may include a local area network, the Internet, any other form of a network, or in any combination thereof, including proprietary private and semi-private networks and public networks. The network may comprise a wired network and/or a wireless network (e.g., a cellular network, wireless local area network, wireless wide area network, some combination thereof, and/or the like).

Having now described an example apparatus for implementing example embodiments, FIG. 3 is a flowchart illustrating example operations of an apparatus 200, according to some example embodiments. The operations of FIG. 3 may be performed by apparatus 200, such as with the service provider computer 106 and/or the like.

As shown by operation 302, apparatus 200 may include means, such as processor 212, memory 214, communication interface 218, and/or the like, for receiving, at a service provider computer 106 and from a prescriber computer 104, a prescription benefit coverage inquiry. The prescription benefit coverage inquiry may be generated by a prescriber, such as a physician and/or other clinical staff, at a prescriber computer 104 and may be associated with a particular patient, such as a patient being examined by the prescriber during the time when the prescription benefit coverage inquiry is generated and provided by the prescriber computer 104. In some examples, a physician may consider multiple different prescription options, and discussing the different options in conjunction with estimated costs with the patient, may assist the physician and patient in determining a preferred prescription option. In this regard, the prescription benefit coverage inquiry may be generated in an effort to provide the patient with cost information associated with a prescribed medication, drug, treatment, and/or the like at the time of prescribing.

All too often, a patient is prescribed a medication at a point of prescribing, such as a physician's office, without knowledge of how or even if the medication is covered under the patient's present insurance plan. These scenarios may lead to the patient being uninformed and blindsided by high or inconvenient costs when fulfilling a prescription later on at a pharmacy or other dispensary. Further, this may lead to consequences such as the patient experiencing frustration, forgoing the prescribed medication, and/or future determent from seeking prescription medications, even in instances when desperately needed. Providing the patient with information regarding the cost of the prescription during the appointment may reduce the likelihood that a patient declines a prescription at the pharmacy due to cost, and therefore may improve the likelihood of the patient adhering to a prescription because the patient has an expectation of the cost of a prescription before visiting the pharmacy.

The prescription benefit coverage inquiry may include information regarding a medication and/or treatment that the prescriber intends to prescribe to the patient. The prescription benefit coverage inquiry may also comprise a variety of information, such as, but not limited to: patient demographic information, such as name, date of birth, age, and/or address, insurance/coverage information such as cardholder name, Cardholder ID and/or other identifier, Group ID and/or Group Information, prescriber information such as Primary Care Provider ID or other identifier (e.g. NPI code), Primary Care Provider Name, Prescriber ID or other identifier (e.g. NPI code, DEA number), patient's Preferred Pharmacy or other Healthcare Provider Information (e.g. store name, chain identifier, store address, etc.), various claim information such as drug, service, or medication identifier (e.g. via National Drug Code (NDC) number), Prescription/Service Reference Number, Date Prescription Written, Diagnosis/Condition, Number of Refills Authorized, and/or the like.

According to certain embodiments, the service provider computer 106 may receive, transmit, and/or process a plurality of prescription benefit coverage inquiries, such as from one or more prescriber computers 104, on a continual and/or ongoing basis and may process such request in real-time or near real-time. The term "near" real-time is used to express that the inquiry may be processed, and a cost estimate may be desired within a fraction of a second, or seconds, from the time the prescription benefit coverage inquiry is submitted.

In operation 304, apparatus 200 may include means, such as processor 212, memory 214, communication interface 218, and/or the like, for transmitting a prescription benefit coverage inquiry to a claims processor computer 108 for processing. In certain embodiments, the claims processor computer 108 may adjudicate or otherwise process the prescription benefit coverage inquiry. For example, the claims processor computer 108 may be associated with the patient's PBM, insurance provider, and/or the like. In some embodiments, the adjudication may comprise a determination of whether the medication associated with the prescription benefit coverage inquiry is covered by the patient's insurance, and may provide additional medication cost information relevant to the patient and/or prescriber.

In operation 305, apparatus 200 may include means, such as processor 212, memory 214, and/or the like, for determining whether a response is received, from the claims processor computer 108, within a predetermine amount of time. In this regard, in certain embodiments, the apparatus 200 may include means, such as processor 212, memory 214, communication interface 218, and/or the like, for monitoring for receipt of a response associated with the prescription benefit coverage inquiry within a predetermined amount of time, or time threshold.

For example, the service provider computer 104 may await a response from the claims processor computer 108 by monitoring or tracking the time it takes to receive a response from the claims processor computer and/or how much time has elapsed since transmitting the response from the service provider computer to the claims processor computer. In this regard, a predetermined amount of time used as a time threshold may be considered a predefined condition. It should be appreciated, however, that the predetermined amount of time and/or any other predefined condition (described below) may be configurable, such as by a user with administrative rights and/or the like. As an example, a predetermined amount of time used as a time threshold may be 0.2 seconds. If a response is determined to have been received by the service provider computer 106 within the time threshold, (e.g., by 0.2 seconds of having transmitted the benefit coverage inquiry to claims processor computer 108), operations proceed to operation 306.

In this regard, the apparatus 200 may include means, such as processor 212, memory 214, communication interface 218, and/or the like, for receiving a response associated with the prescription benefit coverage inquiry. The response may be received, for example, at the service provider computer 106 from a claims processor computer 108. In this regard, the claims processor computer 108 may generate and provide a response associated with the prescription benefit coverage inquiry after adjudication and/or other processing by the claims processor computer.

If it is determined a response has not have been received by the service provider computer 106 within the time threshold, (e.g., by 0.2 seconds of having transmitted the prescription benefit coverage inquiry to claims processor computer 108), referred to as a timeout, or no response is received prescription benefit coverage inquiry, processing may proceed to operation 308, described below. In some examples, the response time may be too slow such that the predefined condition comprising the predetermined amount of time is not satisfied, and/or no response is received at all relating to the prescription benefit coverage inquiry. A response may not be received for any number of reasons, such as, for example, one or more errors on behalf of the claims processor computer 106, one or more errors associated with the prescription benefit coverage inquiry, and/or the like.

In operation 306, apparatus 200 may include means, such as processor 212, memory 214, and/or the like, for determining whether a response received from the claims processor computer 108 is sufficient for providing to the prescriber computer 104, as described in further detail below. According to certain embodiments, a received response may be determined as sufficient for providing to the prescriber computer 104 if it satisfies one or more predefined conditions. The predefined conditions may relate a time constraint condition (described above with respect to the predetermined amount of time and threshold and operation 305) and/or data relevancy condition, described below.

In this regard, receiving a response from the claims processor 108 within the predetermined amount of time does not necessarily mean the response is sufficient for providing to the prescriber computer 104. Responses that are received within the predetermined amount of time may be further analyzed to determine if the data therein satisfies other predefined conditions, such as data relevancy conditions, to determine whether the response is relevant to a patient and/or prescriber.

In certain non-limiting examples, the response may include, one or more fields comprising a patient pay amount field populated with a value returned by the claims processor computer 106, an estimated out of pocket range that the patient can expect to pay, returned by the claims processor computer, a pharmacy name field populated with a pharmacy name corresponding to the submitted service provider ID on the prescription benefit coverage inquiry, a pharmacy street address populated with a pharmacy street address corresponding to the submitted service provider ID on the prescription benefit coverage inquiry, and/or other associated fields.

In this regard, the response may be determined by the service provider computer 106 to be sufficient for providing to the prescriber computer 104 and/or relevant to a patient and/or prescriber if the response comprises a patient pay amount field populated with a value returned by the claims processor computer 106. This value may indicate a cost that the patient may incur when fulfilling a prescription for the medication associated with the prescription benefit coverage inquiry. Additionally, a sufficient response may comprise a status or indication that the medication associated with the prescription benefit coverage inquiry is covered by the patient's pharmacy benefits manager/insurance provider. In one or more embodiments, the determination of a sufficient response may comprise parsing the response to identify if one or more fields comprise values suitable for provision to a user at the prescriber computer 104. For example, the service provider computer 106 may parse the prescription benefit coverage inquiry to determine if the patient pay amount comprises a value greater than or equal to zero, and if so, the response is determined to be sufficient for providing to the prescriber computer 104. If a specific value such as the patient pay amount is NULL, or less than zero, it may be determined that the response is not sufficient for providing to the prescriber computer 104, and processing continues at operation 38. It will be appreciated that any other fields in the response may be analyzed and/or processed relative to a predefined condition, to determine whether the response is sufficient for providing the response to the prescriber computer 104.

In some embodiments, in the event of an erroneous transmission, mishandling of the prescription benefit coverage inquiry by the claims processor computer 108 or other misstep, or if the response includes a status or indication that the medication associated with the prescription benefit coverage inquiry is not covered by the patient's pharmacy benefits manager/insurance provider, the service provider computer 106 may determine that a sufficient response was not received. Another example in which the service provider computer 106 may determine that a sufficient response was not received, may include examples in which the response includes one or more fields (e.g., patient pay amount, estimated cash price range, pharmacy name field, and/or the like) being returned blank or NULL. As another example, example embodiments may determine that a sufficient response was not received if a reject reason field is populated with a rejection reason, such as a rejection reason corresponding to the rejected prescription benefit coverage inquiry (e.g., pricing not available for an identified scenario). Example embodiments may determine that a sufficient response was not received if a reason for service code field is populated with a reject error code, and/or a reason for service description field is populated with an abbreviated description of a corresponding reason for service code. In this regard, due to lacking or missing information in the response from the claims processor computer 108, and/or any of the above described reject-related codes or reasons occurring in the response, the service provider computer 106 may determine that a sufficient response was not received.

The response received from the claims processor computer 108 may be missing information as described above, such as values for a patient pay amount and/or the like. Additionally or alternatively, the response may provide indication of various circumstances in which a patient pay amount and/or other necessary information may be absent from the response such that response is insufficient for providing to the prescriber computer 104. As such, determining an estimated cost range for the prescribed medication associated with the prescription benefit coverage inquiry may be beneficial in helping the prescriber provide a patient with accurate medication cost information, as described in further detail with regard to operation 308. These circumstances may include, but are not limited to, the following indications:

TABLE 1

| | |
|---|---|
| Refill Too Soon | Product Not Covered - Non-Participating Manufacturer |
| Missing Group Number | Product/Service Not Covered for Gender |
| Inactive Group Number | Patient is Not Covered |
| Non-Matched Cardholder ID | Refills are Not Covered |
| Prior Authorization Required | Step Therapy, Alternate Drug Therapy Required Prior to Use of Submitted Product Service ID |
| Product/Service Not Covered | Cost Exceeds Maximum |
| Product Not on Formulary | Days Supply Exceeds Plan Limitation |
| Product/Service Not Covered for Age | Cardholder ID submitted is inactive |

It will be appreciated that operation 306 may be configured and/or modified to define different conditions that should be met for a response to be considered sufficient for providing to the prescriber computer 104. The predefined conditions may be programmed by a developer, and/or configured by a user using user interface 216.

In operation 310, performed if a sufficient response is received within the predetermined amount of time, the service provider computer 106 may transmit the response to the prescriber computer 104 for display to a user, such as a physician, patient, and/or the like. In this regard, apparatus 200 may include means, such as processor 212, memory 214, communication interface 218, and/or the like for providing, or transmitting, a response associated with a prescription benefit coverage inquiry to the prescriber computer 104 or other associated entity for display to a user. In some examples, the response may be forwarded to the prescriber computer 104 as provided by the claims processor computer 108. In certain example embodiments, the service provider computer 106 may modify the response provided by the claims processor computer 108 to include additional information.

Continuing to operation 308, performed when a timeout occurs, or a sufficient response is not received, apparatus 200 may include means, such as processor 212, memory 214, and/or the like, for determining an estimated cost range for the prescribed medication associated with the prescription benefit coverage inquiry. In this regard, in an instance in which a response from the pharmacy claims processor computer 108 is not received or a received response fails to satisfy a predefined condition, a cost range for the prescribed medication may be estimated as described in further detail below with respect to FIG. 4.

FIG. 4 provides operations associated with operation 308 and the process of determining an estimated cost range for the prescribed medication. The service provider computer 106 may determine an estimated cost range for the prescribed medication associated with the prescription benefit coverage inquiry based on historical data.

At operation 400, apparatus 200 may include means, such as processor 212, memory 214, and/or the like, for retrieving historical data comprising prior prescription transactions associated with the prescribed medication. The historical data may be further associated with a time range, pharmacy, state and/or other criteria. For example, the service provider computer 106 may access historical data, such as data comprising prior prescription transactions, via a database 102. As described above, data may be provided to database 102 by one or more pharmacy computers 110 and/or service provider computers 106. These one or more pharmacies may voluntarily provide data directly or indirectly to database 102, such as historical data related to prior prescription transactions that have taken place at each respective pharmacy. In an embodiment, the one or more pharmacies may be taking part in a program wherein data associated with the one or more pharmacies, such as prior prescription transaction data, is supplied to database 102 to provide patients and prescribers with accurate cost information at a point of prescribing. In this regard, example embodiments, such as with processor 212, may search the data within the database 102 and acquire results based on the prescription benefit coverage inquiry.

The prescription benefit coverage inquiry may indicate a preferred pharmacy of a patient, the state in which the preferred pharmacy is located, prescribed medication and/or associated NDC, and/or the like. In some embodiments, the service provider computer 106 may search the database 102 for prior prescription transactions (including NDC & quantity transaction combinations) that have taken place within a predefined time period and are associated with the preferred pharmacy, state of the pharmacy, and prescribed medication. For example, a prescription benefit coverage inquiry may indicate a preferred "Pharmacy A", a state in which the pharmacy is located, such as "Georgia", and a prescribed medication "Medication X". In the event the service provider computer 106 fails to receive a response from the claims processor computer 108, or the response is erroneous and/or lacking required information, the service provider computer 106 may search the database 102 for prior prescription transactions associated with "Pharmacy A" (including pharmacies included in a chain of "Pharmacy A") in Georgia, and "Medication X" that have taken place within a predefined time period, such as, for example, in the previous sixty days. In some examples, the pharmacy computer 110 of the preferred pharmacy indicates what chains of pharmacies for which historical data should be accessed. The service provider computer 106 may then receive one or more results comprising prior prescription transactions that have taken place in the previous sixty days at "Pharmacy A" (including pharmacies related by chain) located in Georgia regarding "Medication X".

In certain embodiments, after the search has been performed and the results of the search are received by service provider computer 106, the service provider computer may then filter the results at operation 401. In this regard, the apparatus 200 may include means, such as processor 212, memory 214, and/or the like, for filtering the historical data so as to exclude one or more types of prescription transactions from consideration based on filtering criteria.

For example, one or more prior prescription transactions within the results that are associated with a compound drug (i.e. a non-FDA-approved combination of two or more drugs tailored to a specific individual's needs) may be excluded, or eliminated, from the results. One or more prior prescription transactions within the results that are associated with a Coordination of Benefits (i.e. two or more insurance plans paying claims for the same patient) may also be excluded from the results. Additionally, one or more prior prescription transactions within the results that are associated with a cash payment (i.e. the recipient paid cash out-of-pocket for medication without assistance from an insurance plan) may also be excluded from the results. As another example, some filtering criteria may include filters to include only cash transactions and to exclude prescription transactions processed by a payor. This may enable example embodiments to provide an estimated cost range for a cash transaction. Further, one or more prior prescription transactions with the results that indicate that a patient associated with the one or more prior prescription transactions were in a deductible stage (i.e. paying toward a deductible prior to an insurance plan assisting) may be excluded from the results. Based on the filtering the historical data so as to exclude one or more types of prescription transactions from consideration, the service provider computer 106 may obtain a filtered set of historical data comprising prior prescription transactions.

At operation 402, the service provider computer 106 may determine an average value based on a paid amount associated with each prescription transaction of the filtered historical data. In this regard, the apparatus 200 may include means, such as processor 212, memory 214, and/or the like, for determining an average value based on a paid amount associated with each of the prescription transactions in the filtered historical data. For example, the service provider computer 106 may determine an average value, such as the mean, of all values associated with the patient pay amount field in each prior prescription transaction within the filtered set of historical data. Thus, the average value may indicate an average amount paid by patients at a pharmacy in a particular state, such as the preferred pharmacy associated with a prescription benefit coverage inquiry, for a prescribed medication, such as the prescribed medication associated with a prescription benefit coverage inquiry, in a predefined period of time. In the example above, the average value may indicate the average amount paid by patients at "Pharmacy A" in Georgia for "Medication X" in the past sixty days.

In an embodiment, the apparatus 200 may include means, such as processor 212, memory 214, and/or the like, for determining a standard deviation or other calculated amount associated with the average value of the filtered historical data. At operation 403, the service provider computer may identify a subset of prescription transactions within one standard deviation or other calculated amount of the average value. In this regard, the apparatus 200 may include means, such as processor 212, memory 214, and/or the like, for identifying a subset of prescription transactions within the filtered historical data that comprise a patient pay amount within one standard deviation of the average value.

The service provider computer may compare each paid amount to a standard deviation associated with the average value. In this regard, the apparatus 200 may include means, such as processor 212, memory 214, and/or the like, for comparing each paid amount to the standard deviation to determine one or more paid amounts that are within a predefined number of standard deviations of the calculated amount. In an embodiment, the service provider computer 106 may compare each patient pay amount in each prior prescription transaction within the filtered set of results to a calculated amount to identify a subset of prior prescription transactions which comprise a patient pay amount within a predefined number of standard deviations (e.g., 1) of the average value. Identification of a subset of prescription transactions within one standard deviation may be performed to ensure enough data is present to accurately provide an estimated cost range. In other words, at operation 404, the service provider computer 106 may determine whether the identified subset of prescription transactions comprises enough prescription transactions to proceed with determining an estimated cost range for the prescribed medication. In this regard, the apparatus 200 may include means, such as processor 212, memory 214, and/or the like, for determining if the number of prescription transactions within the identified subset satisfies a predefined threshold.

In the event that the number of prescription transactions within the identified subset fails to satisfy the predefined threshold, the process may proceed to operation 410. According to some example embodiments, if not enough transactions are present in the filtered historical data that fall within a first predefined number of standard deviations (e.g., one standard deviation) from the average value, example embodiments may determine that there is insufficient historical data for estimating a cost range, or for estimating a cost range with a minimum threshold level of confidence of accuracy, and may provide a message to the prescriber computer 104 indicating that patient benefits and/or an estimated cost range of the prescribed medication is not available. In this regard, the apparatus 200 may include means, such as processor 212, memory 214, and/or the like, for providing a response to the prescriber computer 104 indicating an estimated cost range is not available for the prescribed medication associated with the prescription benefit coverage inquiry.

In the event that the number of prescription transactions within the identified subset satisfies the predefined threshold, the service provider computer 106 may determine that enough data, such as enough prescription transactions, is available to estimate a cost range for the prescribed medication. At operation 406, the apparatus 200 may include means, such as processor 212, memory 214, and/or the like, for including prior prescription transactions comprising paid amounts within a second predefined number of standard deviations of the average value in the subset of prescription transactions. For example, the subset of prior prescription transactions may only comprise prior prescription transactions with a patient pay amount within two standard deviations of the average value. In the above example, the service provider computer 106 may include all prior prescription transactions with a patient pay amount within two standard deviations of the average value in the subset of prior prescription transactions.

At operation 408, once the subset of prior prescription transactions based on the average value has been determined, the service provider computer may determine the estimated cost range of the prescribed medication based on the subset of prescription transactions. In this regard, the apparatus 200 may include means, such as processor 212, memory 214, and/or the like, for determining, from the subset of prescription transactions, the estimated cost range of the prescribed medication that ranges a calculated amount from the average value. A low-end and a high-end of the estimated cost range of the prescribed medication may be amounts that are a predefined number of standard deviations, such as two standard deviations, from the mean in each direction. For example, if the average value is determined to be $50, and the standard deviation is determined to be $7.5, the estimated cost range of the prescribed medication may be determined to be a range from $35 to $65. In other words, continuing with the above example, the patient with a preferred "Pharmacy A" in Georgia that is prescribed "Medication X" may be expected to pay between $35 and $65 for Medication X.

Example embodiments may therefore order the filtered historical transactions by the transactions' respective variances from the average or mean patient payment amount. The estimated cost range for a prescription may then be estimated as the prices that are 2 standard deviations from the left and 2 standard deviations from the right of the average for the copay range.

In this regard, the filtered historical data may be further refined to reduce outliers and/or to focus the data set on data determined to yield an accurate estimated price range of a prescription. For example, outliers such as historical transactions that include erroneous paid amounts, and/or the like, may be eliminated by identifying a subset of the transactions within one or more standard deviations of the average value.

Returning to FIG. 3, in operation 312, the apparatus 200 may include means, such as processor 212, memory 214, communication interface 218, and/or the like, for determining whether the prescription benefit coverage inquiry reflects a government plan. Example embodiments may utilize any information included in the prescription benefit coverage inquiry to determine if the patient is a participant in one or more government-funded healthcare insurance programs, or "government plan." For example, a Medicare or other government healthcare insurance program eligibility file, such as an eligibility file maintained by a transaction facilitator (e.g., Centers for Medicare or and Medicaid Services (CMS)), may be searched for patient identifying information that matches or otherwise corresponds to patient identifying information included in the prescription benefit coverage inquiry. If the patient is covered under a government plan, the patient and/or prescription benefit coverage inquiry may not be eligible for incentives and/or targeted co-pays described in further detail below with respect to operations 314, 316, 317, and/or 319. Said differently, example embodiments may determine the prescription benefit coverage inquiry reflects a government plan, and in response thereto, determine the prescription benefit coverage inquiry is not eligible for an incentive. Accordingly, if the prescription benefit coverage inquiry reflects a government plan, operations 314, 316, 317, and/or 319 may be bypassed in the flowchart of FIG. 3, and processing may continue to operation 320, described below.

However, in operation 312, if example embodiments determine the prescription benefit coverage inquiry does not reflect a government plan, processing may continue to operation 314 to determine if an inventive is available. Instances in which the prescription benefit coverage inquiry does not reflect a government plan may include those in which the patient is enrolled in a commercial plan, such as any insurance or health plan not government-funded. As another example, another instance in which the prescription benefit coverage inquiry does not reflect a government plan includes when a patient is uninsured and/or the patient seeks a cash price for the prescription without submitting a claim to insurance.

In any event, if it is determined the prescription benefit coverage inquiry does not reflect a government plan, in operation 314, the apparatus 200 may include means, such as processor 212, memory 214, communication interface 218, and/or the like, for determining whether an incentive is available, based on the prescription benefit coverage inquiry. An incentive may include, but is not limited to, a coupon, voucher, rebate, discount, loyalty award, or other equivalent non-insurance benefit or the like that is provided, or credited to the patient when the medication is dispensed to the patient. U.S. Pat. No. 10,489,552, "SYSTEMS AND METHODS FOR DETERMINING AND COMMUNICATING PATIENT INCENTIVE INFORMATION TO A PRESCRIBER," describes determining and communicating incentive information, and is hereby incorporated by reference in its entirety. For example, certain drug manufacturers may offer incentives in the form of rebates, payable to a payor associated with the claims processor computer 108, and/or credit to the patient toward the cost of the medication.

In certain embodiments, the incentive may be configured such that an out-of-pocket cost (e.g., co-pay, or cash out-of-pocket cost) is targeted for the patient. A certain drug manufacturer may make a target out-of-pocket cost for a patient to purchase a certain medication, $25, for example.

Determining whether an incentive is available may include processing a variety of conditions based on the prescription benefit coverage inquiry. For example, determining whether an incentive is available may include determining, such as with processor 212, whether a pharmacy associated with the pharmacy computer 110 from which the prescription benefit coverage inquiry was received, is a contracted pharmacy, such as a pharmacy contracted to receive incentive program services, such as coupon and other incentive identification services provided under an eVoucheRx™ program, or other similar program, which may be supported by the service provider computer 106. For example, service provider computer 106 may compare a pharmacy identifier associated with the pharmacy computer 110 to a list of contracted pharmacies to see if a match exists. If a match exists, service provider computer 106 may determine the pharmacy is a contracted pharmacy and further evaluate the prescribed medication, as described in further detail below, to determine if an incentive is available. If the pharmacy is not a contracted pharmacy, and/or the processor 212 determined the pharmacy identifier does not match an identifier on a list of contracted pharmacies, example embodiments determine there is no incentive available, and processing proceeds to operation 320, described in further detail below.

If it is determined the pharmacy is a contracted pharmacy, or if such a determination is not required, example embodiments, such as with processor 212, compare the mediation identifier to a schedule, list, or table of medication identifiers for which coupons, discounts, rebates, or other incentives in an incentive program are available. For example, if a match exists, example embodiments may determine an incentive is available. In certain embodiments, the list may further indicate that an incentive may be available based on the medication identifier, but that other conditions to determine whether the prescription benefit coverage inquiry qualifies for the incentive.

As such, in in operation 316, the apparatus 200 may include means, such as processor 212, memory 214, communication interface 218, and/or the like, for determining whether the prescription benefit coverage inquiry qualifies for the incentive. In certain embodiments, the list of medication identifiers indicating an available incentive may further indicate scenario-based conditions. According to certain embodiments, the scenario-based conditions optionally evaluated before determining if an incentive will be received, may include but are not limited to patient gender, patient zip/postal code, dispensed quantity of medication, historical use of the medication by the patient, including whether the patient has previously or not previously used the medication and whether the patient is adhering to a proper regimen of use of the medication based on the timing of refills. The term "scenario-based conditions" is referenced to indicate the factors are additional beyond the requirements of the pharmacy being a contracted pharmacy and the medication identifier having an associated incentive available. If the scenario-based conditions are met, or no scenario-based conditions are required to be evaluated to determine qualification for the incentive, example embodiments continue processing at operation 317. If the prescription benefit coverage inquiry does not qualify for the incentive based on not satisfying any of the additional required conditions, processing may continue at operation 320.

Continuing with operation 317, performed in response to determining the prescription benefit coverage inquiry qualifies for an incentive, the apparatus 200 may include means, such as processor 212, memory 214, communication interface 218, and/or the like for determining a targeted out-of-pocket cost. Example embodiments may determine a targeted out-of-pocket cost by the patient by querying or accessing a list of targeted out-of-pocket costs, based on the medication identifier. Information regarding incentive amounts may be provided to the service provider computer 106 by a pharmaceutical manufacturer or other sponsor of the incentive, which may be performed in a separate process such that the service provider computer 106 maintains the information. For example, a pharmaceutical manufacturer or other sponsor of the incentive may transmit a file or other records of targeted out-of-pocket costs for certain medication, which example embodiments may reference in a list or database in conjunction with performance of operation 317.

At operation 319, in an instance the incentive is available, apparatus 200 may include means, such as processor 212, memory 214, communication interface 218, and/or the like, for generating an incentive notification message. The incentive notification message may comprise a notification that an incentive may be available, such that a user of the prescriber computer 104 may understand why the targeted out-of-pocket cost is displayed in addition to the estimate cost range (described in further detail below with regard to operation 320).

At operation 320, the apparatus 200 may include means, such as processor 212, memory 214, communication interface 218, and/or the like, for providing the estimated cost range for the prescribed medication to the prescriber computer 104. In scenarios in which a targeted out-of-pocket cost is determined (317), and/or an incentive notification message is generated (319), the targeted out-of-pocket cost and/or incentive notification message may also be transmitted to the prescriber computer 104. The targeted out-of-pocket cost and/or incentive notification message may be appended to a response including the estimated cost range, and/or may be transmitted separately from the estimated cost range.

Accordingly, example embodiments, such as with processor 212, memory 214, user interface 216, communication interface 218 and/or the like, may cause display of the estimated cost range, incentive notification message, and/or targeted out-of-pocket cost, on the prescriber computer 104. For example, the response displayed may indicate that an estimate price range of a certain medication is $25-$40, and that due to an incentive or drug manufacturer rebate, or other voucher, a patient may be able to obtain the medication for $25. A physician or other prescriber may therefore see the information and discuss it with a patient.

In certain embodiments in which a response to a prescription benefit coverage inquiry was received by the service provider computer 106 from the claims processor 108, but was determined to not be sufficient for providing to the prescriber computer 104 due to lacking required information, the service provider computer 106, in addition to providing the estimated cost range, targeted out-of-pocket cost, and/or incentive notification message, may also provide information relating to the received response. In other words, a prescriber may receive information regarding a potential prescription claim based on the response provided by the claims processor computer 108. For example, the prescriber may be notified that the estimated cost range and/or targeted out-of-pocket cost is not based on an adjudicated claim.

As another example, in certain embodiments, a response from the claims processor computer 108 may comprise information indicating that prior authorization may be required for a prescribed medication associated with the prescription benefit coverage inquiry and may not comprise any type of medication cost information because the prior authorization has not been obtained. According to example embodiments, in such a scenario, the service provider computer 106 may provide the message indicative of the requirement for prior authorization, as well as provide an estimated cost range, assuming the preauthorization is obtained, to the prescriber computer 104 to ensure the prescriber and patient have all necessary information. In this regard, certain example embodiments append an estimated cost range calculated by the service provider computer 106 to a response received from claims processor 108 to provide more meaningful information to the prescriber computer 104.

Once the estimated cost range, incentive notification message, and/or targeted out-of-pocket cost are provided to the prescriber computer 104, a prescriber may review the information on a user interface and provide the estimated cost range, indication of an incentive, and/or targeted out-of-pocket to the patient associated with the prescription benefit coverage inquiry. Thus, in the event a response from the patient's pharmacy benefits manager is not received or lacking required information, the patient may be well informed of an estimated range for the cost of the prescribed medication, and/or the targeted out-of-pocket cost, at the time of prescribing, alleviating the patient from being blindsided of unforeseen costs when attempting to fulfill the prescription at a preferred pharmacy. As an example, a patient may suggest that the estimated cost range and/or targeted out-of-pocket cost is too burdensome for the patient, and in turn the prescriber, such as the patient's physician, may suggest or prescribe alternative medications, and in some embodiments, provide another prescription benefit coverage inquiry associated with the alternative medication in order to provide the patient with additional cost information for the alternative medication.

Example embodiments, such as those including but not limited to those performing operations described above, may therefore provide technical improvements over existing service provider systems, including that attempt to provide responses from the claims processor computer 108. As described herein, prior systems may not provide any pricing information in the event that a response to a prescription benefit coverage inquiry is not provided by a claims processor computer 108, or in the event that a response is erroneous and/or lacking required information, such as a patient pay amount. In such systems, processing resources, such as memory and/or processing power may be utilized in receiving and submitting subsequent inquiries and responses by the service provider computer 106 and/or prescriber computer 104 only to be wasted in the event that a response from a claims processor computer 108 is never received or erroneously provided. Additional processing resources, such as memory used to store and track problem tickets, may also be required to facilitate the correction of such issues.

Example embodiments provide technical improvements to such systems by implementing the apparatus 200 such that estimated cost ranges of prescribed medication and/or targeted out-of-pocket cost may be calculated and determined in real-time or near real-time as the physician prescribes a medication for a patient. The term "near" real-time is used to express that a cost estimate may be provided at the prescriber computer 104 within a fraction of a second, or seconds, from the time the prescription benefit coverage inquiry is submitted. The technical challenges in providing this real-time feedback are increased by the evolving complexities of healthcare transactions and their associated processing by claims processing computers 108, and the uncertainty or inconsistency of response quality and response time associated therewith. The challenges are further increased by the ever-increasing volume of data received from pharmacies and/or claims processors. Example embodiments leverage the historical data in a manner described herein that provides efficient, and accurate cost estimates and/or targeted out-of-pocket cost for patients and physicians at the point of service.

The solutions provided by example embodiments therefore improve the usage of processing resources, and additionally or alternatively improve the functioning of the service provider computer 106 by reducing and/or eliminating erroneous responses and reducing and/or eliminating instances in which prescribers and patients are left without cost information when responses are not provided by a claims processor computer 108. Additionally, processing resources are further conserved by not necessarily determining an estimated cost range and/or targeted out-of-pocket cost for every submission of a prescription benefit coverage inquiry, but by selectively determining an estimated cost range under certain circumstances, such as when a response from a claims processor computer 108 is not received or is insufficient for providing to the prescriber computer 104.

Similarly, example embodiments may reduce and/or eliminate the need for prescription benefit coverage inquiry resubmissions, and/or the like, caused by users such as prescribers not understanding why a response was never received, and resubmitting identical prescription benefit coverage inquiries in hopes of receiving a proper response. This may therefore reduce the resources expended, such as memory and/or processing power, that may otherwise be required to facilitate the resubmission (and possibly numerous resubmissions) of the same prescription benefit coverage inquiry, as well as the associated rerouting, and reprocessing of the resubmitted transaction(s) throughout the various components described herein. Likewise, example embodiments may reduce processing resources otherwise expensed on extensive research, custom queries, and/or the like, when cost estimates for prescriptions cannot otherwise be obtained. Accordingly, example embodiments described herein further improve the technical efficiency of systems implementing and/or employing such embodiments.

It will be appreciated that the figures are each provided as examples and should not be construed to narrow the scope or spirit of the disclosure in any way. In this regard, the scope of the disclosure encompasses many potential embodiments in addition to those illustrated and described herein. Numerous other configurations may also be used to implement embodiments of the present invention.

FIGS. 3-4 illustrate operations of a method, apparatus, and computer program product according to some example embodiments. It will be understood that each operation of the flowchart or diagrams, and combinations of operations in the flowchart or diagrams, may be implemented by various means, such as hardware and/or a computer program product comprising one or more computer-readable mediums having computer readable program instructions stored thereon. For example, one or more of the procedures described herein may be embodied by computer program instructions of a computer program product. In this regard, the computer program product(s) which embody the procedures described herein may comprise one or more memory devices of a computing device (for example, memory 214) storing instructions executable by a processor in the computing device (for example, by processor 212). In some example embodiments, the computer program instructions of the computer program product(s) which embody the procedures described above may be stored by memory devices of a plurality of computing devices. As will be appreciated, any such computer program product may be loaded onto a computer or other programmable apparatus (for example, apparatus 200) to produce a machine, such that the computer program product including the instructions which execute on the computer or other programmable apparatus creates means for implementing the functions specified in the flowchart block(s). Further, the computer program product may comprise one or more computer-readable memories on which the computer program instructions may be stored such that the one or more computer-readable memories can direct a computer or other programmable apparatus to function in a particular manner, such that the computer program product may comprise an article of manufacture which implements the function specified in the flowchart block(s). The computer program instructions of one or more computer program products may also be loaded onto a computer or other programmable apparatus (for example, apparatus 200 and/or other apparatus) to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. An apparatus comprising one or more processors and at least one memory including computer program code, that when executed by the at least one or more processors, causes the one or more processors to perform steps of:

storing a time threshold and a history of prescription transactions;

receiving, from a prescriber computer, a prescription benefit coverage inquiry associated with a patient and a prescribed medication;

transmitting the prescription benefit coverage inquiry to a pharmacy claims processor computer;

monitoring a network for receipt of a response associated with the prescription benefit coverage inquiry from the pharmacy claims processor computer;

determining whether a response from the pharmacy claims processor computer is received within the time threshold;

determining that an incentive is available based on the prescription benefit coverage inquiry;

based on a determination that the response from the pharmacy claims processor computer is not received within the time threshold, and further based on the stored history of prescription transactions, generating an estimated cost range for the prescribed medication and transmitting the generated cost range and an incentive amount to the prescriber computer; and based on a determination that the response from the pharmacy claims processor is received within the time threshold, transmitting the incentive amount and the received response to the prescriber computer, wherein the response includes a pay amount field comprising a value.

2. The apparatus of claim 1, wherein the computer program code, when executed by the one or more processors, further causes, in response to determining that the incentive is available, the one or more processors to perform steps of:

generating an incentive notification message, wherein the incentive notification message comprises a notification that an incentive may be available; and transmitting the incentive notification message to the prescriber computer.

3. The apparatus of claim 1, wherein determining whether the incentive is available comprises:

receiving an indication of a medication identifier associated with the prescribed medication;

determining whether a match exists by comparing the medication identifier to a list of medication identifiers representing medications for which an incentive is available; and determining a match exists, and in response thereto, determining the incentive is available and that the prescription benefit coverage inquiry qualifies for the incentive.

4. The apparatus of claim 1, wherein generating the estimated cost range comprises:

determining an average value based on a paid amount associated with each of the prescription transactions in a historical data;

identifying a subset of prescription transactions from the historical data based on the average value; and from the subset of prescription transactions, determining the estimated cost range of the prescribed medication that is within a range of the average value.

5. The apparatus of claim 1, wherein the computer program code, when executed by the one or more processors, further causes the one or more processors to perform a step of:

determining that another prescription benefit coverage inquiry reflects a government plan, and in response thereto, determining another prescription benefit coverage inquiry is not eligible for an incentive.

6. The apparatus of claim 1, wherein providing the estimated cost range and a targeted out-of-pocket cost for the prescribed medication to the prescriber computer is performed in real-time or near real-time relative to receiving a prescription benefit coverage inquiry associated with a patient and a prescribed medication.

7. A computer program product comprising at least one non-transitory computer-readable storage medium having computer-executable program code instructions stored therein, that when executed by one or more processors, cause the one or more processors to perform steps of:

storing a time threshold and a history of prescription transactions;

receiving, from a prescriber computer, a prescription benefit coverage inquiry associated with a patient and a prescribed medication;

transmitting the prescription benefit coverage inquiry to a pharmacy claims processor computer;

monitoring a network for receipt of a response associated with the prescription benefit coverage inquiry from the pharmacy claims processor computer;

determining whether a response from the pharmacy claims processor computer is received within the time threshold;

determining that an incentive is available based on the prescription benefit coverage inquiry;

based on a determination that the response from the pharmacy claims processor computer is not received within the time threshold, and further based on the stored history of prescription transactions generating an estimated cost range for the prescribed medication and transmitting the generated cost range and an incentive amount to the prescriber computer; and based on a determination that the response from the pharmacy claims processor is received within the time threshold, transmitting the incentive amount and the received response to the prescriber computer, wherein the response includes a pay amount field comprising a value.

8. The computer program product of claim 7, wherein the computer-executable program code instructions that when executed by the one or more processors, in response to determining that the incentive is available, further cause the one or more processors to perform steps of:

generating an incentive notification message, wherein the incentive notification message comprises a notification that an incentive may be available; and transmitting the incentive notification message to the prescriber computer.

9. The computer program product of claim 7, wherein determining whether the incentive is available comprises:

receiving an indication of a medication identifier associated with the prescribed medication;

determining whether a match exists by comparing the medication identifier to a list of medication identifiers representing medications for which an incentive is available; and determining a match exists, and in response thereto, determining the incentive is available and that the prescription benefit coverage inquiry qualifies for the incentive.

10. The computer program product of claim 7, wherein the computer-executable program code instructions that when executed by the one or more processors, further causes the one or more processors to perform a step of:

determining that another prescription benefit coverage inquiry reflects a government plan, and in response thereto, determining another prescription benefit coverage inquiry is not eligible for an incentive.

11. The computer program product of claim 7, wherein providing the estimated cost range for the prescribed medication to the prescriber computer is performed in real-time or near real-time relative to receiving a prescription benefit coverage inquiry associated with a patient and a prescribed medication.

\* \* \* \* \*